(12) United States Patent
Hart-Cooper et al.

(10) Patent No.: US 11,723,362 B2
(45) Date of Patent: *Aug. 15, 2023

(54) BROAD-SPECTRUM SYNERGISTIC ANTIMICROBIAL COMPOSITIONS

(71) Applicants: The United States of America, as represented by the Secretary of Agriculture, Washington, DC (US); Method Products, PBC, San Francisco, CA (US)

(72) Inventors: William M. Hart-Cooper, Richmond, CA (US); William J. Orts, Burlingame, CA (US); Anna C. Kundmann, Pleasanton, CA (US); Diana M. Franquivillanueva, Concord, CA (US); Kaj Johnson, Sausalito, CA (US); Dirk Develter, Madelgem (BE); James D. McManus, Tracy, CA (US)

(73) Assignees: -The United States of America, as represented by The Secretary of Agriculture, Washington, DC (US); Method Products, PBC, San Francisco, CA (US)

( * ) Notice: Subject to any disclaimer, the term of this patent is extended or adjusted under 35 U.S.C. 154(b) by 49 days.

This patent is subject to a terminal disclaimer.

(21) Appl. No.: 17/024,273

(22) Filed: Sep. 17, 2020

(65) Prior Publication Data
US 2021/0084896 A1    Mar. 25, 2021

Related U.S. Application Data

(60) Provisional application No. 62/902,630, filed on Sep. 19, 2019.

(51) Int. Cl.
*A01N 37/18* (2006.01)
*A01N 47/44* (2006.01)

(52) U.S. Cl.
CPC ............ *A01N 37/18* (2013.01); *A01N 47/44* (2013.01)

(58) Field of Classification Search
None
See application file for complete search history.

(56) References Cited

U.S. PATENT DOCUMENTS

2018/0303100 A1* 10/2018 Hart-Cooper .......... A01N 47/44
2018/0320116 A1* 11/2018 Swanson .............. C11D 17/049

FOREIGN PATENT DOCUMENTS

WO    WO2019/002391    *    1/2019
WO    WO 2019/005064    *    1/2019

OTHER PUBLICATIONS

Honest, "What is caprylhydroxamic acid", https://www.honest.com/blog/wellness/ingredients/what-is-caprylhydroxamic-acid/13775.html, published Jul. 30, 2018. (Year: 2018).*

* cited by examiner

*Primary Examiner* — Melissa L Fisher
(74) *Attorney, Agent, or Firm* — John D. Fado; Maria Restrepo-Hartwig

(57) ABSTRACT

Compositions comprising synergistic blends of organic acids and hydrazones and methods of reducing bacterial and fungal contamination using the blends are disclosed.

25 Claims, 6 Drawing Sheets

Caprylhydroxamic acid or

1: R = H
2: R = Me
3: R = Et
4: R = $^n$Pr
5: R = $^i$Pr
6: R = $^n$Bu

Hydroxamic acids

4-alkylbenzaldehyde    Aminoguanidium

7: R' = H
8: R' = $^n$Octyl

Aryl guanylhydrazones

BROAD-SPECTRUM SYNERGISTIC ANTIMICROBIAL COMPOSITIONS

CROSS-REFERENCE TO RELATED APPLICATIONS

This application claims priority to U.S. Provisional Patent Application No. 62/902,630, filed Sep. 19, 2019. The content of this provisional patent application is hereby expressly incorporated by reference in its entirety.

FIELD OF THE INVENTION

The disclosed invention relates generally to novel and synergistic antimicrobial compositions. Specifically, the invention relates to compositions including an organic acid (hydroxamic, carboxylic) and a hydrazone that together exhibit complementary synergistic fungicidal and bactericidal activity in surfactant-containing formulas.

BACKGROUND OF THE INVENTION

Broad spectrum antimicrobial compositions are an essential category of biocide, and are used as antibiotic treatments, disinfectants, sanitizers, handwashes, and preservatives, among others. Traditional antimicrobial agents used as antibiotics, disinfectants, and preservatives have recently come under scrutiny for their human and environmental hazards. Preservatives for non-food products (e.g. home and personal care products, paints, coatings) have historically been, for example, formaldehyde, tetra-alkyl (or benzyl) ammonium compounds, or isothiazolinone-based, all of which are contact allergens and exhibit high aquatic toxicity, in addition to many other hazards. These human and environmental hazards of current antimicrobials, coupled with the growing threat of antibiotic resistance, has created the need for improved products and strategies to achieve microbial control.

Applications for ionic surfactant-compatible, broad spectrum antimicrobial compositions are numerous, including topical antibiotics for livestock, pesticide compositions for crops, disinfectants and cleaners for food processing and preservatives for food and non-food agricultural products. Preservatives for non-food products (e.g. home and personal care products, paints, coatings) have historically been formaldehyde or isothiazolinone-based, both of which are contact allergens and exhibit high aquatic toxicity, in addition to many other hazards such as carcinogenicity and reproductive and developmental hazards. While cationic antimicrobials (e.g., traditional quaternary ammonium compounds, bisbiguanides, etc.) exhibit good performance in nonionic surfactant-containing formulas, they are often deactivated and generally incompatible in formulas containing anionic and amphoteric surfactants, which constitute a large category of consumer, industrial and agricultural products. Preservation of these formulations at mild pH (6-8) is particularly challenging because this pH is hospitable to microbial growth and causes deactivation of traditional preservatives like organic acids.

There thus exists an urgent ongoing industrial need for substitute antimicrobials that are potent, broad-spectrum, and safe. There is a particular need for novel antimicrobials that are stable in a variety of surfactant formulations, disinfectants, odor control, and manufacturing plant sanitizers to replace conventional antimicrobials such as traditional cationic compounds, isothiazolinones, and formaldehyde-releasers.

SUMMARY OF THE INVENTION

To address these industrial challenges, the present invention provides novel bio-based synergistic antimicrobial compositions that are effective in non-food products using components that are low in toxicity and environmentally friendly. The inventive compositions showed surprising synergism against a combination of microorganisms with utility in agriculture and industry as broad-spectrum disinfectants, preservatives, industrial sanitization, and pathogen treatments, among other applications. In a preferred aspect, the invention relates to compositions including a blend of at least one organic acid and at least one hydrazone that exhibits antimicrobial biological activity in a variety of applications. In another aspect, the invention relates to methods of reducing bacterial and fungal contamination by applying an effective amount of the inventive composition to a designated area or object.

It is an advantage of the invention to provide novel antimicrobial compositions useful in an array of industrial applications such as livestock treatments, industrial cleaners, cleaning concentrates, detergents, medical devices, personal care products, hand cleaners, pesticide compositions for crops, disinfectants for food processing, and preservatives for food and non-food agricultural products, as well as an array of other categories.

It is another advantage of the present invention to provide novel highly potent, broad spectrum antimicrobial compositions that function in challenging anionic and amphoteric surfactant-containing formulas.

It is a further advantage of the present invention to provide biodegradable broad-spectrum antimicrobial compositions that do not persist in the environment and are much less toxic to aquatic organisms than conventional compositions.

It is yet another advantage of the present invention to provide novel renewably sourced antimicrobial compositions that minimize the risk for development of antimicrobial resistance because they are non-sensitizing at the low concentrations utilized and thereby less prone to create resistant strains in the environment.

An additional advantage of the invention is to provide novel cationic antimicrobial compositions for home and personal care formulas that are not deactivated when blended with anionic and amphoteric surfactants.

It is a further advantage of the invention is to provide novel antimicrobial compositions that extend compatibility with different types of surfactants, provide broad-spectrum activity against many different types of microorganisms, increase the rate of antimicrobial activity, and extend pH range functionality.

This summary is provided to introduce a selection of concepts in a simplified form that are further described below in the detailed description. This summary is not intended to identify all key or essential features of the claimed subject matter, nor is it intended to limit the scope of the claimed subject matter.

BRIEF DESCRIPTION OF THE DRAWINGS

FIG. 3A presents the results for *E. coli*. FIG. 3B presents the results for *S. aureus*. FIG. 3B presents the results for *P. aeruginosa*. FIG. 3D presents the results for *A. brasiliensis*. FIG. 3E presents the results for *B. cepacia*. FIG. 3F presents the results for *C. albicans*. The Y axis shows the $Log_{10}$ CFU/mL. The X axis shows the time in days. Solid lines indicate the detection limits; large dash and dot lines indicate data for unpreserved spray cleaner base; dashed lines indicate data for spray cleaner base plus 0.2 wt % CG; dotted lines indicate data for spray cleaner base plus 0.1 wt. % CG plus 0.1 wt. % sodium benzoate.

FIG. 4A shows the hydroxamic acids: caprylhydroxamic acid or hydroxamic acid where in 1 R is H, in 2 R is methyl, in 3 R is ethyl, in 4 R is n-propyl, in 5 R is isopropyl, and in 6 R is butyl. FIG. 4B shows the aryl guanylhydrazones, where in 7 R' is H and in 8 R' is Octyl.

DETAILED DESCRIPTION OF THE INVENTION

Figure 1:
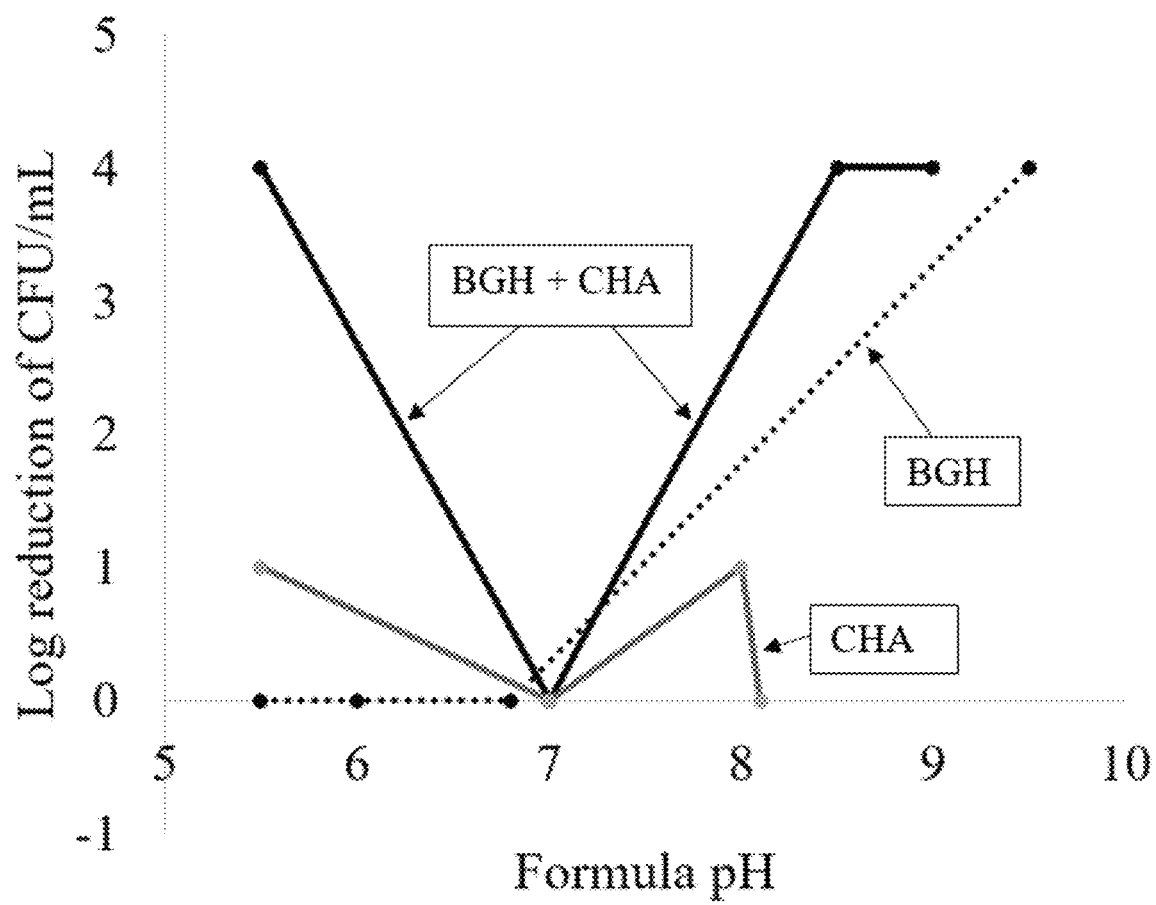
FIG. 1 illustrates the fungicidal properties of a handwash formula containing the inventive composition as further explained in the examples below. The Y axis presents the log reduction of cell forming units per mL (CFU/mL). The X axis presents the pH of the different formulas. Data for benzaldehyde guanylhydrazone 7+CHA is shown with black lines (BGH+CHA); data for benzaldehyde guanylhydrazone 7 (BGH) is shown with dotted lines; data for CHA alone is shown with grey lines.

Unless herein defined otherwise, all technical and scientific terms used herein generally have the same meaning as commonly understood by one of ordinary skill in the art to which this invention belongs. The definitions and terminology herein described for embodiments may or may not be used in capitalized as well as singular or plural form herein and are intended to be used as a guide for one of ordinary skill in the art to make and use the invention and are not intended to limit the scope of the claimed invention. Mention of trade names or commercial products herein is solely for the purpose of providing specific information or examples and does not imply recommendation or endorsement of such products.

As used in the description of the invention and the appended claims, the singular forms "a," "an," and "the" are intended to include the plural forms as well, unless the context clearly indicates otherwise.

The term "active agent" refers to a compound or composition which exhibits substantial biological activity. For example, the biological activity could be inhibitory (e.g., <1-log increase over 1-4 weeks), sanitizing (e.g., about 3-log reduction over 10 min), or disinfecting (e.g., about 4-log reduction over 10 min).

The term "antimicrobial" refers to an active agent that has biological activity against microorganisms such as bacteria, fungi, viruses, etc. and creates an environment where such microorganisms would be reduced or eliminated. Related terms are specifically directed to certain types of microorganisms such as "antibacterial," "antifungal," "antiviral," and the like.

The term "biological activity" refers to the strength or ability of a compound or composition to prevent, inhibit, treat, reduce, or eliminate the growth of at least one microorganism.

The term "carrier" refers to a gel or an encapsulating matrix or agent used to "carry" the active agent to a targeted site of activation without negatively affecting functionality. Dilution with a carrier does not significantly dilute the end-effect of the active agent, rather it prevents waste by minimizing excessive application of active ingredients The term "complex" or "complexation" refers to a molecular entity product formed by a reversible ionic association or covalent bond of a plurality of starting molecular entities. The reversible nature of the product and starting molecular entities may exist as a spontaneous formation of self-assembly and disassembly within a medium containing the molecular entities.

The term "consisting essentially of" excludes additional method steps or composition components that substantially interfere with the intended activity of the methods or compositions of the invention and can be readily determined by those skilled in the art (e.g., from a consideration of this specification or practice of the invention disclosed herein). This term may be substituted for inclusive terms such as "comprising" or "including" to more narrowly define any of the disclosed embodiments or combinations/sub-combinations thereof. Furthermore, the exclusive term "consisting" is also understood to be substitutable for these inclusive terms in alternative forms of the disclosed embodiments.

The term "effective amount" of a compound or property as provided herein is meant such amount as is capable of performing the function of the compound or property for which an effective amount is expressed. As is pointed out herein, the exact amount required will vary from process to process, depending on recognized variables such as the compounds employed and various internal and external conditions observed as would be interpreted by one of ordinary skill in the art. Thus, it is may not be possible to specify an exact "effective amount," though preferred ranges have been provided herein. An appropriate effective amount may be determined, however, by one of ordinary skill in the art using only routine experimentation.

The term "hydroxamic acid" refers to a class of compounds having the general formula:

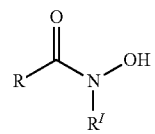

where R is aryl, benzyl, or alkyl, and wherein $R^I$ is H, aryl, benzyl, or alkyl.

The term "hydrazone" refers to a class of compounds having the general formula:

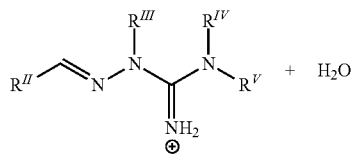

where $R^{II}$, $R^{III}$, and $R^{IV}$ are independently H, aryl, or alkyl; and $R^V$ is H, aryl, alkyl, $NCHR^{II}$, or $NH_2$. These compounds may exist as a self-assembled complexation at equilibrium with starting materials of an aminoguanidine and an aldehyde.

The term "microorganism" refers to any bacterium, fungus (e.g., mold, yeast, mushroom, toadstool, etc.), algae (e.g., unicellular, multicellular), protozoan (e.g., free-living, parasitic), or other unicellular organism, or a virus (e.g., enveloped, non-enveloped) as well colonies, biofilms, cultures, populations, infections, etc. formed therefrom which may or may not be pathogenic.

The term "optional" or "optionally" means that the subsequently described event or circumstance may or may not occur, and that the description includes instances and embodiments in which said event or circumstance occurs and instances and embodiments where it does not. For example, the phrase "optionally comprising a self-assembled complex" means that the composition may or may not contain a self-assembled complex and that this description includes compositions that contain and do not contain a self-assemble complex.

The present invention provides a composition comprising a blend of at least one organic acid and at least one hydrazone. In embodiments, the organic acid includes at least one carboxylic acid and/or at least one hydroxamic acid or a blend thereof. Hydroxamic acids and hydrazones (e.g., aminoguanidine-aldehyde hydrazones) are typically non-sensitizing at the levels used in the inventive composition, biodegradable, and much less toxic to aquatic organisms than traditional antimicrobials. This invention solves the general problem of achieving broad spectrum antimicrobial properties and more specifically, effectiveness at low concentration levels in challenging non-food products using bio-based, low toxicity chemicals that do not persist in the environment. The hydroxamic acids (antifungal properties) and hydrazones (antibacterial properties) herein described are narrow spectrum antimicrobials when used alone; however, it was surprisingly discovered that when combined they are broad spectrum and exhibit synergistic activity. The compositions described herein were developed with human and environmental health as a top priority, as all components can be renewably sourced and are designed to degrade rapidly in the environment, thereby minimizing the risk for antimicrobial resistance to develop.

In embodiments, the composition includes a hydroxamic acid component having the general formula:

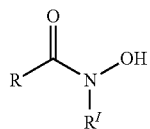

where R is aryl, benzyl, or alkyl, and wherein $R^I$ is H, aryl, benzyl, or alkyl. In embodiments, the aryl substituent may include mono-, di- or tri-alkyl substituted aryl groups at the 2, 3, 4, 5, and 6-positions, or 4-alkyl (i.e. Me, Et, Pr, iPr, Bu, iBu, s-Bu, t-Bu, Pentyl, Hexyl, Heptyl) substituted aryl groups. In embodiments, the alkyl substituent may include Me, Et, Pr, iPr, Bu, iBu, s-Bu, t-Bu, as well as branched or linear configurations of Pentyl, Hexyl, Heptyl, Octyl. Additional alternatives for the hydroxamic acid component of the inventive composition may include one or a plurality of the following hydroxamic acids: salicylhydroxamic acid; N-hydroxysuccinimide; benzhydroxamic acid; O-methylhydroxylamine HCl; O-benzylhydroxylamine HCl; N-benzylhydroxylamine HCl; O-tert-butylhydroxylamine HCl; acetohydroxamic acid; suberohydroxamic acid; O-ethylhydroxylamine HCl; O-phenylhydroxylamine HCl; N-hydroxyoctanamide (or caprylhydroxamic acid); N-hydroxymaleimide; N-hydroxydecanamide, N-hydroxynonamide, N-hydroxyheptanamide, N-hydroxyhexanamide.

In an embodiment, the hydroxamic acid has the following formula (4-alkyl-benzhydroxamic acid):

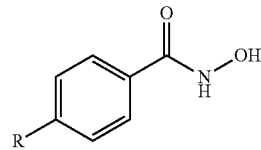

where R is H, methyl, ethyl, propyl, isopropyl, or butyl.

In embodiments, any combinations or ratios of any of the disclosed organic acids may also be used in the inventive composition. For example, benzhydroxamic acid, caprylhydroxamic acid, and 4-alkyl-benzhydroxamic acids could be mixed in ratios about 1:1:1, or up to about 10:1:1, or up to about 1:10:1, or up to about 1:1:10, or up to about 10:10:1, or up to about 1:10:10.

In embodiments, the composition includes a hydrazone having the general formula:

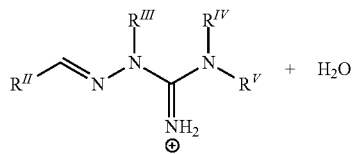

where $R^{II}$, $R^{III}$, and $R^{IV}$ are independently H, aryl, or alkyl; and $R^V$ is H, aryl, alkyl, $NCHR^{II}$ (indicating a second or subsequent hydrazone molecule attached at $R^V$), or $NH_2$. In embodiments, the aryl substituent may include mono-, di- or tri-alkyl substituted aryl groups at the 2, 3, 4, 5, and 6-positions, or 4-alkyl (i.e. Me, Et, Pr, iPr, Bu, iBu, s-Bu, t-Bu, Pentyl, Hexyl, Heptyl) substituted aryl groups. In embodiments, the alkyl substituent may include Me, Et, Pr, iPr, Bu, iBu, s-Bu, t-Bu, as well as branched or linear configurations of Pentyl, Hexyl, Heptyl, Octyl.

The hydrazone component of the inventive composition is formed from an aldehyde component and a guanidine component. In embodiments, the aldehyde component can generally be any aldehyde as selected by a skilled artisan. For example, the aldehyde could be $R^{II}$=CHO where $R^{II}$ is the same as in the hydrazone structure. Exemplary aldehydes for a component in an active agent may include glyoxal, glutaraldehyde, benzaldehyde, phthalaldehyde, terephthalaldehyde, isophthalaldehyde, benzene-1,3,5-tricarboxaldehyde, 2-bromoisophthalaldehyde, 4-tBu-2,6-diformylphenol, 4-Me-2,6-diformylphenol, 3,5-diformyl-2-propoxyphenylboronic acid, 2,5-thiophenedialdehyde, and 2,5-furandialdehyde. Additional alternatives for the aldehyde include one or more of alkyl-substituted benzaldehyde; an aldehyde molecule having three or more aldehyde functional groups; 2,3,4-trihydroxybenzaldehyde; 3,4,5-trihydroxybenzaldehyde; syringaldehyde; vanillin acetate; vanillin; isovanillin; o-vanillin; 2,4,6-trimethoxybenzaldehyde; 4-hydroxybenzaldehyde; 2,6-dimethoxybenzaldehyde; 2,5-dimethoxybenzaldehyde; ethyl vanillin; o-anisaldehyde; e, p-tolualdehyde; or cuminaldehyde.

In embodiments, the guanidine could be represented by the general formula:

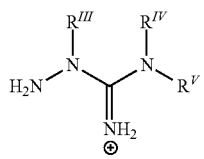

where $R^{III}$, $R^{IV}$, and $R^{V}$ are the same as the hydrazone structure. The guanidine component may include an aminoguanidine and/or a molecule that has two or more amine functional groups (e.g., 1,3-aminoguanidine).

In embodiments, the inventive composition includes a complex that is formed by self-assembly of an aldehyde component and a guanidine component. The complex may be formed through an ionic interaction or a covalent bond (e.g., hydrazone bond) between the aldehyde component and the guanidine component. For example, the hydrazone may include a self-assembled complexation of an aminoguanidine and an aldehyde having the following the formula:

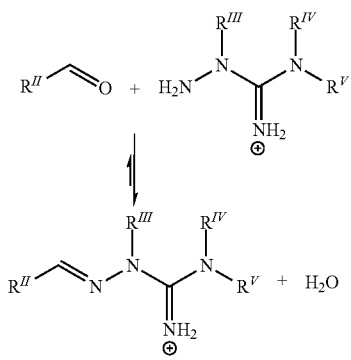

where the $R^{II-V}$ substituents are described above. In another example, the hydrazone may include a self-assembled complexation of an aminoguanidine and an aldehyde having the following the formula:

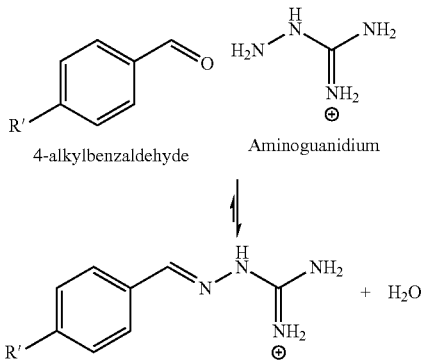

where RI is H or octyl. The aminoguanidine, the aldehyde, and the hydrazone may exist in equilibrium in the blend according to various embodiments.

In embodiments, the inventive composition includes at least one of cuminaldehyde guanyhydrazone (CG), 4-isopropyl-3-methylphenol (43IMP), or Bis(cuminaldehyde) guanylhydrazone, having the following formulas:

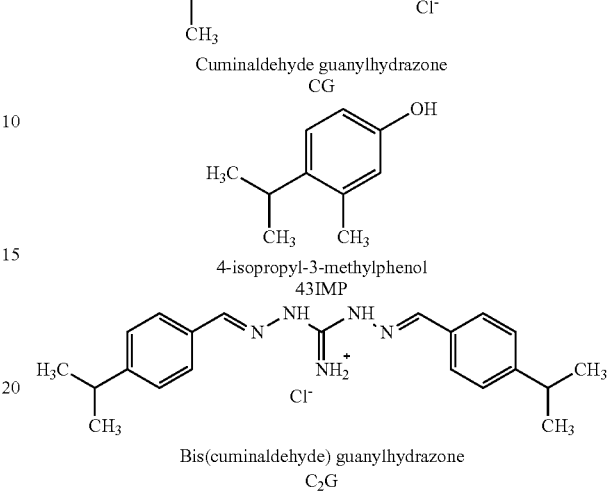

In embodiments, the combined weight percentage within a formulation of the one or more organic acid and the one or more hydrazone blend is less than about 2 wt %, or less than about 1 wt %, or less than about 0.5 wt %. In embodiments, the organic acid component and hydrazone component are present in the blend (with amounts adjusted to total 100 wt %) from about 0.00001 wt % to about 100 wt % and from about 100% to about 0.00001 wt %, respectively, or from about 0.005 wt % to about 5 wt % and from about 5 wt % to about 0.005 wt %, respectively, or from about 0.01 wt % to about 1 wt % and from about 1 wt % to about 0.01 wt %, respectively, or from about 0.1 wt % to about 1 wt % and from about 1 wt % to about 0.1 wt %, respectively. In embodiments, the ratio of the one or more organic acids and the one or more hydrazones in the blend is from about 100:1 to about 1:100, or from about 10:1 to about 1:10, or from about 1:2 to about 2:1, or about 1:1.

Formulas where the inventive composition has particular relevance and provide unexpected and surprising compatibility include, for example, ionic or amphoteric surfactant-containing formulas (e.g., foamy and non-foamy handwashes; dishwashing liquids; household cleaning sprays; laundry detergents; personal care products including lotions, body washes, and shampoos; cleaning concentrates; spray and non-spray cleaners such as dilutable concentrates; adhesives and coatings; industrial cleaners including sanitizers, disinfectants, odor control agents; livestock treatments including hoof dips, utter dips, oral antibiotics, topical antiseptics, odor control, feed additives; medical devices; pesticide compositions for crops; disinfectants for food processing; and preservatives for food and non-food agricultural products; the like; etc.). Not intending to be theory-bound, the aminoguanidine-aldehyde is a cationic amphiphile, and it is thought that the observed synergistic antimicrobial activity arises from the ability of this substance to increase membrane permeabilities of microorganisms, which could enhance the antifungal activity of hydroxamic acid by facilitating its passage into the cell. This synergy allows low levels (less than 0.5 wt %) of the composition to be added to such formulas for efficacy, which is a comparable to current more toxic antimicrobials. While cationic antimicrobials generally exhibit good performance in nonionic surfactant-containing formulas, they are often deactivated by and are thus incompatible in formulas containing anionic and amphoteric surfactants, which constitute a large category of consumer, industrial, and agricultural products. Preservation of these formulations at mild pH (e.g., 6-8) is challenging because this pH is hospitable to microbial growth and causes deactivation of traditional preservatives like organic acids. This invention overcomes formula compatibility by pairing a strongly antifungal hydroxamic acid with a potent antibacterial guanylhydrazone. While the guanylhydrazone would typically be rendered ineffective by certain ingredients or contaminants (e.g. certain surfactants and minerals), this loss in activity is compensated for by the hydroxamic acid, thereby enabling surprising broad-spectrum activity to be obtained.

In embodiments, the invention is in concentrated form that is soluble in liquid additives such as propane diol, ethanol, glycerin, or water which may aid in the manufacture of the blend and also enhance formula compatibility. The inventive composition may also be provided as a solid form which would be diluted by an end user to achieve the concentrations disclosed herein.

In embodiments, the invention is a method of reducing bacterial and fungal contamination. The inventive composition is effective against one type or combinations of bacteria such as *Escherichia coli, Pseudomonas aeruginosa, Staphylococcus aureus, Listeria monocytogenes, Salmonella, Burkholderia cepacia, Clostridium difficile, Streptococcus, Vibrio, Bacillus, Campylobacter, Chlamydia, Listeria, Neisseria, Treponema*, among others. The composition is also effective against one type or combinations of fungal species such as *Aspergillus brasiliensis, Aspergillus fumigatus. Candida albicans, Candida auris*, among others. The method includes applying an effective amount of the inventive composition to a designated area or object. The composition may be an ingredient in a formulation and present in the formulation in a concentration range as further discussed herein.

In embodiments, the invention is a method of producing an antimicrobial and antifungal active agent. The method includes combining a guanidine molecule, an aldehyde molecule, and a hydroxamic acid molecule in solution. The bioactivity of the combination of the guanidine molecule, the aldehyde molecule, and the hydroxamic acid molecule is synergistic and greater than the sum of the individual bioactivities of the guanidine molecule, the bioactivity of the aldehyde molecule, and the bioactivity of the hydroxamic acid molecules.

In embodiments, certain compounds may interfere with the intended activity of the inventive composition. It should be appreciated that a skilled artisan may choose to exclude compounds such as cocoamidopropyl betaines, sodium lauryl sulfate, sodium laureth sulfate, and the like under certain conditions. Not intending to be theory-bound, anionic or amphoteric surfactants of certain molecular weight and carbon chain length may, for example associate with the inventive composition, sequestering it and reducing its activity.

Other compounds may be added to the composition provided they do not substantially interfere with the intended activity and efficacy of the composition, whether or not a compound interferes with activity and/or efficacy can be determined, for example, by the procedures utilized herein. Such other compounds may include one or more of, for example, film-forming polymers, surfactants, chelators, fragrances, and solvents. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement. The following examples are intended only to further illustrate the invention and are not intended in any way to limit the scope of the invention as defined by the claims.

EXAMPLE 1

This example illustrates preparation of the hydroxamic acid component of the inventive composition (see e.g., Premachandran, R. et al., PCT Publication No. WO/2016/164555; Synergistic preservative compositions, 2018). Aroyl chlorides were prepared as a precursor to the hydroxamic acid. A 10 mmol solution of aroyl acid was prepared in 20 mL chloroform and 12 mmol oxalyl chloride (Sigma-Aldrich, St. Louis, Mo.) was added. Dimethylformamide (DMF, 99.8%, Sigma-Aldrich) was added as a catalyst and the reaction was stirred overnight (e.g., 18 h). This reaction was estimated to have produced 10 mmol of the aroyl acid chloride of the substituted aroyl acid. The reaction for each aroyl chloride was continued with the addition of ~22 mmol $NH_2OH.HCl$ (hydroxylamine hydrochloride; Fisher Scientific, Fair Lawn, N.J.) and ~50 mmol triethylamine (TEA; ≥99%, Sigma-Aldrich), and was stirred for at least 7 hours. The resulting solution was washed 3 times with equivalent volume of 1 N HCl and dried with $MgSO_4$. Dried chloroform was evaporated to precipitate the arylhydroxamic acid product. Approximately 1.4 g and 1.1 g respectively of 4-N-propylbenzhydroxamic acid and 4-isopropylbenzhydroxamic acid were recovered, respectively. Each of the dried products was flaky and opaque with a slight orange color; the 4-N-propyl product was of a darker shade. This procedure was also followed for 4-alkylbenzoyl chloride (96%, Sigma-Aldrich) at a ratio of 5 mmol of the aryl acid chloride to ~11 mmol $NH_2OH.HCl$ and ~25 mmol of TEA. Approximately 1 g of 4-N-pentylbenzhydroxamic acid was recovered which had a waxy texture with a light orange tint. Compounds were characterized using $^1H$ NMR and $^{13}C$ NMR (Spin Solve 80, Magritek, Malvern, Pa.).

Aminoguanidine-aldehyde hydrazones were prepared according to previously reported protocols (see e.g., Grady, R. W. et al., *Mol. Biochem. Parasitol.* 19, 231-240, 1986; Beumer, R. & Klock, J., PCT Publication No. WO/2006/029818, Cosmetic compositions containing a hydroxamic acid compound optionally in combination with a retinoid, 2006). An exemplary general procedure was performed as follows. 170 g of aminoguanidine hydrochloride was dissolved in 145 g of deionized water and stirred until homogenous (~20 min). 222 g of cuminaldehyde was added to this solution in an Erlenmeyer flask with stirring. The initially heterogenous mixture was heated to 50° C. and stirred vigorously for 30 min, during which the reaction mixture evolved heat and the temperature rose to 100° C. as the solution became a transparent yellow. The viscous yellow resulting liquid contained 73% guanylhydrazone and 27% water, as apparent by 1H NMR. No byproducts were observed. Although aldehydes may produce strong odors or fragrances, functionalization with aminoguanidine typically renders the resulting guanylhydrazone odorless. The fragrance or odor of an aldehyde mixture can thus be controlled by the careful addition of aminoguanidine. The bis(cuminaldehyde) guanylhydrazone $C_2G$ was prepared in an analogous manner, with two molar equivalents of cuminaldehyde being treated with one equivalent of diaminoguanidine hydrochloride.

EXAMPLE 2

This example illustrates the preparation of testing parameters for antimicrobial activity of components of the inventive composition and related compositions for comparison. For this testing, minimum inhibitory concentrations (MIC) were obtained as follows (see e.g., Buckley, H. L. et al. Design and Testing of Safer, More Effective Preservatives for Consumer Products. ACS Sustain. Chem. Eng. 5, 4320-4331, 2017). Mold were grown and minimum inhibitory tests performed as previously reported (see e.g., Buckley, H. L. et al. ACS Sustain. Chem. Eng. 5, 4320-4331, 2017). Microbes were grown on Mueller-Hinton agar (MHA, Sigma-Aldrich, St. Louis, Mo.) for 7 days until heavy sporulation was present. Spores from two agar plates were captured in sterile phosphate-buffered saline (PBS) using a sterile swab. Spores were enumerated by serial dilution in Dey-Engley neutralizing broth (DEB; Sigma-Aldrich) and spread plating on MHA. A typical spore stock was determined to contain ~$2\times10^7$ spores/mL. Bacteria were grown in MH broth for 24 h at 37° C., enumerated by plating, and diluted to the desired concentration as indicated.

To test the various compounds, a foamy hand soap base formula was made with sodium lauryl sulfate (SLS, 2.4% w/w; Sulfochem SLS-PHP [30% active], The Lubrizol Corporation, Wickliffe, Ohio) and cocoamidopropyl betaine (CAPB, 1.2% w/w; Mackam 35 [30% active], Solvay S.A, Brussels, Belgium) in deionized water and sterilized by filtration (0.22 μm, PVDF; VWR, Radnor, Pa.). All test formulas were adjusted to the desired pH using citric acid and/or NaOH. All tubes were inoculated with 250 μL of spore inoculum (described above) to a total volume of 5 mL, for a final spore concentration of ~$1\times10^6$ spores/mL in each tube. All tubes were kept at room temperature (~21-22° C.) for 3 weeks. About 100 μL of each inoculated foamy hand soap mixture was diluted 1:10 in DEB and 100 μL of this dilution was spread plated on MHA at several time points (e.g. 3 d, 7 d, 13 d, 18 d, and 20 d). Plates were incubated at room temperature for 3-5 days for mold (1-2 days for bacteria) and colonies enumerated.

Preservative challenge testing (USP-51). The protocol for the preservative challenge testing followed the US Pharmacopeia Chapter 51 (USP 51). Under the USP 51 protocol, the test organisms are *Candida albicans* (ATCC No. 10231), *Aspergillus brasiliensis* (also referred to as *A. niger*) (ATCC No. 16404), *Escherichia coli* (ATCC No. 8739), *Pseudomonas aeruginosa* (ATCC No. 9027), and *Staphylococcus aureus* (ATCC No. 6538). To access the potency of a preservative in a personal care product formula, microorganisms were added separately to a sample of the product formula, such that their final concentrations were between 1.00E+05 and 1.00E+06 CFU (colony forming units)/mL of product. The inoculated personal care product formulas were incubated at specific temperatures (relative to the organism) and plated over the course of two weeks. During plating, the number of colony-forming units (CFU's) were counted to determine the number of viable microbial cells still present in the solution. Antimicrobial effectiveness is determined by logarithmic reductions in growth over time.

Figure 4A:
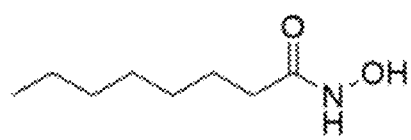
FIG. 4A and FIG. 4B depict some molecules tested in the instant application and the number given to each compound.
Figure 4A:
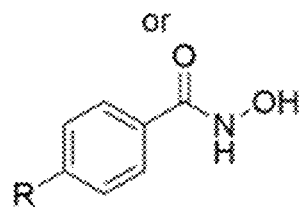
Figure 4B:
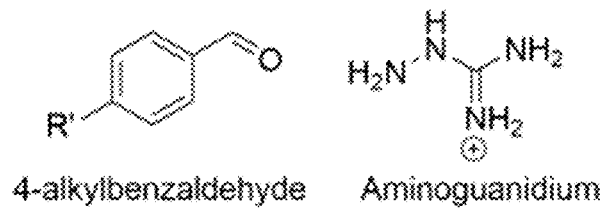
Figure 4B:
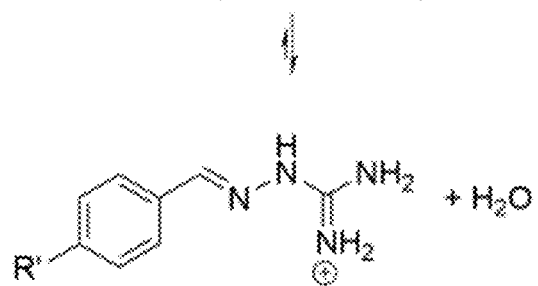

Hydroxamic acids and derivatives tested in the instant application are depicted in FIG. 4A and FIG. 4B. This figure indicates the numbers given to each of the different compounds, and indicated in Table 1, below.

To assess the antimicrobial activity of hydroxamic acids and derivatives, the inhibitory properties of commercially available hydroxylamines and hydroxamic acids were compared to their alcohol and carboxylic acid analogues diluted in Mueller-Hinton broth at pH 7.4 (Table 1).

TABLE 1

Antimicrobial performance of hydroxylamines, hydroxamic acids, alcohols, and carboxylic acids

| | | MIC wt % | | | | |
| --- | --- | --- | --- | --- | --- | --- |
| Entry | Substance | S. aureus | P. aeruginosa | A. brasiliensis | E. coli | C. albicans |
| 1 | Salicylhydroxamic acid | 0.03 | 0.06 | 0.5 | 0.2 | 0.5 |
| 2 | N-hydroxysuccinimide | 0.5 | 0.5 | >0.5 | >0.5 | n.d. |
| 3 | Benzhydroxamic acid (1) | 0.06 | 0.1 | 0.02 | 0.5 | 0.03 |
| 4 | O-methylhydroxylamine HCl | 0.06 | 0.1 | 0.1 | 0.2 | 0.5 |
| 5 | O-benzylhydroxylamine HCl | 0.2 | 0.2 | 0.2 | 0.2 | 0.5 |
| 6 | N-benzylhydroxylamine HCl | 0.5 | 0.2 | 0.2 | 0.5 | 0.5 |
| 7 | O-tert-butylhydroxylamine HCl | 0.1 | 0.2 | 0.5 | 0.5 | 0.5 |
| 8 | Acetohydroxamic acid | 0.5 | 0.5 | 0.5 | 0.5 | 0.2 |
| 9 | Suberohydroxamic acid | 0.5 | 0.5 | 0.5 | >0.5 | 0.5 |
| 10 | O-ethylhydroxylamine HCl | 0.1 | 0.1 | 0.1 | 0.1 | 0.2 |
| 11 | O-phenylhydroxylamine HCl | >0.5 | 0.2 | 0.06 | 0.3 | 0.1 |
| 12 | Caprylhydroxamic acid (CHA) | 0.2 | 0.5 | 0.03 | 0.1 | 0.03 |
| 13 | Salicylic acid | 0.1 | 0.2 | 0.5 | 0.2 | 0.5 |
| 14 | Benzoic acid | 0.2 | 0.2 | 0.2 | 0.2 | 0.2 |
| 15 | Methanol | 20 | 20 | 0.5 | n.d. | 20 |
| 16 | Benzyl alcohol | 0.5 | 0.2 | 0.5 | 0.5 | 0.5 |
| 17 | t-Butanol | 5 | 20 | >0.5 | >0.5 | 0.5 |
| 18 | Acetic acid | 0.06 | 0.06 | 0.2 | 0.1 | 0.2 |
| 19 | Ethanol | 10 | 10 | 0.47 | n.d. | 10 |
| 20 | Phenol | 0.2 | 0.2 | 0.1 | >0.5 | 0.2 |
| 21 | Caprylic acid | 0.5 | 0.5 | 0.5 | 0.5 | 0.5 |

Carboxylic acids were more effective against bacteria than fungi, which is consistent with fungi's relatively enhanced ability to regulate their internal pH. Alcohols were generally ineffective unless moderately hydrophobic (benzyl alcohol). Hydroxylamines tended to exhibit low to moderate efficacy, except for O-phenylhydroxylamine. Moderately hydrophobic hydroxamic acids (caprylhydroxamic acid, benzhydroxamic acid) were the most potent antifungals (*A. brasilensis, C. albicans*) yet were less effective against bacteria. These experiments demonstrated the utility of simple, hydrophobic hydroxamic acids as antifungal agents.

Several aryl derivatives of benzhydroxamic acid were also tested. Based on previous studies and the low antifungal activity of salicylhydroxamic acid (see Table 1—w/w indicates weight ratios of the first and second components listed). Increasing the hydrophobicity of benzhydroxamic acid derivatives resulted in good antifungal activity and moderate to low antibacterial inhibition (Table 2, entries 1-7). In contrast to caprylhydroxamic acid, which required heating and stirring to solubilize, arylhydroxamic acids 1-6 exhibited rapid dissolution at room temperature with minimal agitation. This result is consistent with greater water solubility of aromatics relative to aliphatic substances of similar weight and atom composition (see e.g., Polak, J. & Lu, B. C.-Y. *Can. J. Chem.* 51, 4018-4023, 1973).

TABLE 2

Minimum inhibitory concentrations of hydroxamic acids and AG-benzaldehyde in Mueller-Hinton broth, pH 7.4

| Entry | Substance or combination | A. brasiliensis | P. aeruginosa |
|---|---|---|---|
| 1 | Benzhydroxamic acid 1 | 0.02 | 0.1 |
| 2 | 4-methylbenzhydroxamic acid 2 | 0.02 | 0.3 |
| 3 | 4-ethylbenzhydroxamic acid 3 | 0.06 | 0.5 |
| 4 | 4-n-propylbenzhydroxamic acid 4 | 0.02 | n.d. |
| 5 | 4-isopropylbenzhydroxamic acid 5 | 0.04 | n.d. |
| 6 | 4-n-butylbenzhydroxamic acid 6 | 0.008 | 0.1 |
| 7 | Caprylhydroxamic acid (CHA) | 0.03 | 0.5 |
| 8 | Benzaldehyde guanylhydrazone 7 | n.d. | 0.06 |
| 9 | 4-n-octylbenzaldehyde guanylhydrazone 8 | 0.002 | n.d. |
| 10 | Benzaldehyde guanylhydrazone 7 + 4-ethylbenzhydroxamic acid 3 (4:5 w/w) | 0.06 | 0.1 |
| 11 | Benzaldehyde guanylhydrazone 7 + 4-methylbenzhydroxamic acid 2 (4:5 w/w) | 0.03 | 0.06 |
| 12 | Benzaldehyde guanylhydrazone 7 + 4-n-butylbenzhydroxamic acid 6 (4:5 w/w) | 0.007 | 0.06 |
| 13 | Benzaldehyde guanylhydrazone 7 + Caprylhydroxamic acid (1:2 w/w) | 0.01 | 0.06 |
| 14 | 4-n-octylbenzaldehyde guanylhydrazone 8 + 4-n-propylbenzhydroxamic acid 4 (1:2 w/w) | 0.007 | n.d. |
| 15 | 4-n-octylbenzaldehyde guanylhydrazone 8 + 4-isopropylbenzhydroxamic acid 5 (1:2 w/w) | 0.01 | n.d. | n.d.: not determined.

Guanylhydrazones 7 and 8, which represent a class of broad-spectrum antimicrobials, alone and in combination with hydroxamic acids were evaluated. Owing to their reversible nature, these guanylhydrazones are designed to dissociate and degrade rapidly after use. MIC levels of hydroxamic acid/guanylhydrazone combinations were within experimental error to the sum of their parts. Antimicrobial activity against the Gram-negative bacteria *Pseudomonas aeruginosa* ATCC 9027 was achieved by combining hydroxamic acids with guanylhydrazone 7, indicating compatibility between these two functional classes (see Table 2).

The preservative activity of a hydroxamic acid/guanylhydrazone combination was compared to other antimicrobial mixtures in an ionic surfactant-containing formula. Analogous to previously reported cationic-anionic associations (see e.g., Asnacios, A., et al., *Macromolecules* 29, 7412-7417, 1996; Goddard, E. D. & Hannan, R. B. *J. Colloid Interface Sci.* 55, 73-79, 1976; Sohrabi, B., et al., *J. Phys. Chem. B* 112, 14869-14876, 2008), it was observed that the antifungal activities of guanylhydrazones were attenuated in a hand wash formula (HW) containing the anionic surfactant sodium lauryl sulfate (SLS, 2.4%) and amphoteric surfactant cocoamidopropyl betaine. Not intending to be bound by theory, it was suspected that the strong inhibitory properties of benzhydroxamic acid may compensate for this loss of antifungal activity. The fungicidal properties of a mixture of benzhydroxamic acid and guanylhydrazone (1+7) was compared to commercial antimicrobials representing different functional classes (Table 3). After treatment of chemical combinations with high loadings of *A. brasiliensis* ($10^7$ CFU/mL), low fungicidal activity of all combinations was observed except for those containing benzhydroxamic acid. These results suggested that benzhydroxamic acid could effectively preserve this formula against fungi and is compatible with guanylhydrazone 7.

TABLE 3

Fungicidal activity of HW containing Benzaldehyde guanylhydrazone 7 paired with other antimicrobials, pH 7.0

| | Log Reduction | |
|---|---|---|
| Substance or combination | Day 5 | Day 12 |
| Propyl gallate (0.5%) | 1 | 1 |
| Propyl gallate (0.5%) + Benzaldehyde guanylhydrazone 7 (0.4%) | 1 | 1 |
| Caprylyl Glycol (0.5%) | 0 | 1 |
| Caprylyl Glycol (0.5%) + Benzaldehyde guanylhydrazone 7 (0.4%) | 0 | 2 |
| Benzhydroxamic acid 1 (0.5%) | 1 | 4 |
| Benzhydroxamic acid 1 (0.5%) + Benzaldehyde guanylhydrazone 7 (0.4%) | 1 | 4 |
| Phenoxyethanol (0.5%) | 0 | 1 |
| Phenoxyethanol (0.5%) + Benzaldehyde guanylhydrazone 7 (0.4%) | 1 | 2 |
| Sorbitan caprylate (0.5%) | n.d. | 0 |
| Sorbitan caprylate (0.5%) + Benzaldehyde guanylhydrazone 7 (0.4%) | 0 | 1 |

Based on the promising results of the compounds 1,7 hydroxamic acid/guanylhydrazone combination, the performance of derivatives representing these two functional classes was evaluated. Fungicidal activity was achieved for hydroxamic acids alone and in combination with guanylhydrazones (Table 4). In the presence of SLS/CAPB, guanylhydrazones alone were not effective against *A. brasiliensis* yet retained high activity against *P. aeruginosa* (Table 5). Good bactericidal activity was observed when 4-methyl and 4-ethylbenzhydroxamic acids (2, 3) were combined with 7. A combination containing 4-butylbenzhydroxamic acid 6 and 7, while inhibitory (e.g., Table 2, entry 12), was not bactericidal. While not intending to be bound by theory, it was speculated that the loss of bactericidal activity in the latter case may have been driven by antagonistic associations between the relatively hydrophobic 4-butylbenzhydroxamic acid 6 and 7. These substances would dissociate upon dilution, as during an MIC determination.

TABLE 4

Antifungal activity of single hydroxamic acids, guanylhydrazones and combinations in ionic surfactant base formula (HW, pH 7.0)

| Entry | Substance or combination | Concentration (wt %) | Log reduction Week 1 | Log reduction Week 2 |
|---|---|---|---|---|
| 1 | Benzaldehyde guanyl-hydrazone 7 | 0.4 | n.d. | none |
| 2 | Benzhydroxamic acid 1 | 0.5 | 1 | 4 (day 12) |
| 3 | Benzhydroxamic acid 1 + Benzaldehyde guanyl-hydrazone 7 | 0.5/0.4 | 1 | 4 (day 12) |
| 4 | 4-methylbenzhydroxamic acid 2 | 0.2 | 4 | 4 |
| 5 | 4-methylbenzhydroxamic acid 2 + Benzaldehyde guanylhydrazone 7 | 0.5/0.4 | 4 | 4 |
| 6 | 4-ethylbenzhydroxamic acid 3 | 0.5 | 4 | 4 |
| 7 | 4-ethylbenzhydroxamic acid 3 + Benzaldehyde guanylhydrazone 7 | 0.5/0.4 | 4 | 4 |
| 8 | 4-ethylbenzhydroxamic acid 3 | 0.2 | 4 | 1 |
| 9 | 4-ethylbenzhydroxamic acid 3 + Benzaldehyde guanylhydrazone 7 | 0.2/0.2 | 4 | 2 |
| 10 | 4-n-butylbenzhydroxamic acid 6 | 0.4 | 4 | none |
| 11 | 4-n-butylbenzhydroxamic acid 6 + Benzaldehyde guanylhydrazone 7 | 0.5/0.4 | 4 | 4 |
| 12 | 4-n-butylbenzhydroxamic acid 6 + Benzaldehyde guanylhydrazone 7 | 0.4/0.2 | 4 | 2 |
| 13 | 4-n-butylbenzhydroxamic acid 6 + Benzaldehyde guanylhydrazone 7 | 0.2/0.1 | 4 | 1 |

Inoculation: *Aspergillus brasiliensis* ATCC 16404, $1 \times 10^6$ CFU/mL; 25° C.

TABLE 5

Bactericidal activity of arylhydroxamic acids alone and in combination with AG-benzaldehyde (HW, pH 7.0)

| Substance or combination | Day 3 Log Reduction | Day 10 Log Reduction |
|---|---|---|
| 4-ethylbenzhydroxamic acid 3 (0.2%) | 1 | 0 |
| 4-ethylbenzhydroxamic acid 3 (0.2%) + Benzaldehyde guanylhydrazone 7 (0.2%) | 4 | 4 |
| 4-methylbenzhydroxamic acid 2 (0.2%) | 2 | 4 |
| 4-methylbenzhydroxamic acid 2 (0.2%) + Benzaldehyde guanylhydrazone 7 (0.2%) | 4 | 4 |
| 4-n-butylbenzhydroxamic acid 6 (0.4%) | 0 | 0 |
| 4-n-butylbenzhydroxamic acid 6 (0.4) + Benzaldehyde guanylhydrazone 7 (0.2%) | 0 | 0 |
| 4-n-butylbenzhydroxamic acid 6 (0.2%) + Benzaldehyde guanylhydrazone 7 (0.1%) | 0 | 0 |
| Benzaldehyde guanylhydrazone 7 (0.1%) | 4 | 4 |

Inoculation: *Pseudomonas aeruginosa* ATCC 9027, $1 \times 10^6$ CFU/ml; 37° C.

EXAMPLE 3

This example illustrates the surprising synergistic antimicrobial activity of the inventive composition and related compositions for comparison tested on two of the most persistent microorganisms tested in the USP 51 protocol: *A. brasiliensis* (ATCC No. 16404) and *P. aeruginosa* (ATCC NO. 9027). The effect of pH on antifungal properties of a HW formula containing 0.4% 7 and 0.5% CHA, alone and in combination, was then evaluated under a high fungal load ($10^7$ CFU/mL). Moderate to poor performance was observed with CHA over the entire pH range (0-1 log reduction). 7 alone also exhibited poor performance, except at high pH. Good performance was observed with formulas containing the 7+CHA combination at pH 5.5, 8.5, and 9.0; with low performance at pH 7.0 (Table 6). Without intending to be bound by theory, it was suspected that the poor performance of the combination at neutral pH results from the milder conditions of this formula, which is more encouraging to mold growth.

TABLE 6

USP-51 Test Results for Anionic, Amphoteric Surfactant-Containing Hand Wash

| Entry | Substance code | Contact time | Data description | Organism P. aeruginosa 9027 | Organism A. brasiliensis 16404 |
|---|---|---|---|---|---|
| 1 | Unpreserved HW pH 6 | Time zero | CFU/mL | 1.50E+06 | 1.00E+06 |
| | | Day 6 | CFU/mL | <5.00E+01 | 8.80E+05 |
| | | | Log10 Reduction | >4.48 | 0.06 |
| | | Day 14 | CFU/mL | <5.00E+01 | 5.30E+05 |
| | | | Log10 Reduction | >4.48 | 0.06 |
| 2 | HW with Benzaldehyde guanylhydrazone 7 0.4% 7 pH 6 | Time zero | CFU/mL | 1.50E+06 | 1.00E+06 |
| | | Day 6 | CFU/mL | <5.00E+01 | 4.50E+05 |
| | | | Log10 Reduction | >4.48 | 0.35 |
| | | Day 14 | CFU/mL | <5.00E+01 | 5.05E+05 |
| | | | Log10 Reduction | >4.48 | 0.30 |

TABLE 6-continued

USP-51 Test Results for Anionic, Amphoteric Surfactant-Containing Hand Wash

| | | | | Organism | |
| --- | --- | --- | --- | --- | --- |
| Entry | Substance code | Contact time | Data description | P. aeruginosa 9027 | A. brasiliensis 16404 |
| 3 | HW with CHA 0.5% CHA pH 6 | Time zero | CFU/mL | 1.50E+06 | 1.00E+06 |
| | | Day 6 | CFU/mL | <5.00E+01 | 5.75E+03 |
| | | | Log10 Reduction | >4.48 | 2.24 |
| | | Day 14 | CFU/mL | <5.00E+01 | <5.00E+01 |
| | | | Log10 Reduction | >4.48 | >4.30 |
| 4 | HW with Benzaldehyde guanylhydrazone 7 and CHA 0.2% 7 0.5% CHA pH 6 | Time zero | CFU/mL | 1.50E+06 | 1.00E+06 |
| | | Day 6 | CFU/mL | <5.00E+01 | <5.00E+01 |
| | | | Log10 Reduction | >4.48 | >4.30 |
| | | Day 14 | CFU/mL | 5.00E+01 | <5.00E+01 |
| | | | Log10 Reduction | >4.48 | >4.30 |

Synergistic antifungal activity was observed with three of the hydroxamic acid/guanylhydrazone combinations in HW formula (CHA+7, 4+8, 1+8). While 7 and CHA alone exhibited low to moderate fungicidal activity in formula, in combination total killing was observed (Table 6 and FIG. 1). FIG. 1 in particular shows the fungicidal properties of HW containing 0.4% AG-benzaldehyde, 0.5% CHA, and a combination from pH 5.5-9.5 (plated six days after inoculation; inoculum $10^7$ CFU/mL *Aspergillus brasiliensis* ATCC 16404). The antifungal properties of this combination of the inventive composition was observed to be surprisingly synergistic in the rate of spore killing, as the log reduction of the combination (>4.30) was far greater than the sum of its parts (0.35 and 2.24 at day 6; Table 6). Synergy of comparable magnitude between 8 and 4 as well as 1 was observed (Tables 7 & 8). Compound 5, an isomer of 4, did not have any apparent synergy in combination with 8 yet nonetheless showed its effectiveness as a fungicidal preservative.

TABLE 7

CFU/mL over 3-week incubation of hand soap formulas, pH 7.0

| | Incubation Time | | | | |
| --- | --- | --- | --- | --- | --- |
| Active ingredient | 3 d | 7 d | 13 d | 18 d | 20 d |
| Neg Control | >2.5 × $10^4$ | >2.5 × $10^4$ | >2.5 × $10^4$ | >2.5 × $10^4$ | >2.5 × $10^4$ |
| 4-n-octylbenzaldehyde guanylhydrazone 8 | >2.5 × $10^4$ | >2.5 × $10^4$ | >2.5 × $10^4$ | >2.5 × $10^4$ | >2.5 × $10^4$ |
| 4-n-propylbenzhydroxamic acid 4 | >2.5 × $10^4$ | >2.2 × $10^4$ | 5.0 × $10^2$ | 1.5 × $10^2$ | <5.0 × $10^1$ |
| 4-n-propylbenzhydroxarnic acid 4 + 4-n-octylbenzaldehyde guanylhydrazone 8 | >2.5 × $10^4$ | 3.5 × $10^3$ | <5.0 × $10^1$ | <5.0 × $10^1$ | <5.0 × $10^1$ |
| 4-isopropyibenzhydroxamic acid 5 | >2.5 × $10^4$ | 1.0 × $10^4$ | 1.0 × $10^2$ | <5.0 × $10^1$ | <5.0 × $10^1$ |
| 4-isopropylbenzhydroxamic acid 5 + 4- 4-n-octylbenzaldehyde guanylhydrazone 8 | >2.5 × $10^4$ | 1.4 × $10^4$ | 5.0 × $10^1$ | 5.0 × $10^1$ | <5.0 × $10^1$ |

$^a$0.3 wt % 8, 0.4% hydroxamic acid 4, 5; 5.0 × $10^1$ was the minimum detection limit.

TABLE 8

CFU/mL of hand soap formulas (pH 7.0) after 7 d contact time

| | Organism | |
| --- | --- | --- |
| Active ingredient | A. brasiliensis 16404 | P. aeruginosa 9027 |
| Benzhydroxamic acid 1 | 1 × $10^3$ | 2 × $10^4$ |
| 4-n-octylbenzaldehyde guanylhydrazone 8 | >2 × $10^4$ | >2 × $10^4$ |
| Benzhydroxamic acid 1 + 4-n-octylbenzaldehyde guanylhydrazone 8 | 2 × $10^2$ | 2 × $10^2$ |

0.2 wt % 8, 0.4% 1

EXAMPLE 4

Figure 2:
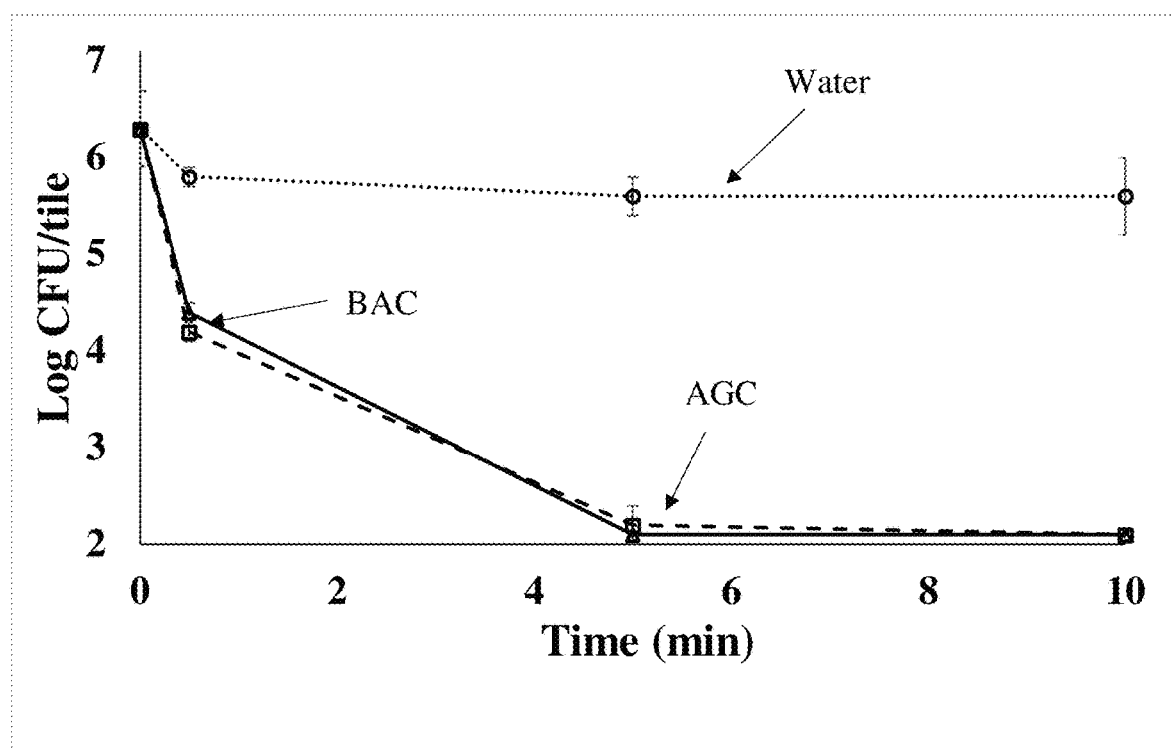
FIG. 2 shows the surface disinfection properties of an exemplary formulation for the inventive composition. The Y axis presents the Log CFU/tile. The X axis presents the time in minutes. A dotted line shows the data obtained for water alone (Water); a dashed line shows the data obtained for CG; and a solid line shows the data obtained for BAC.
Figure 3A:
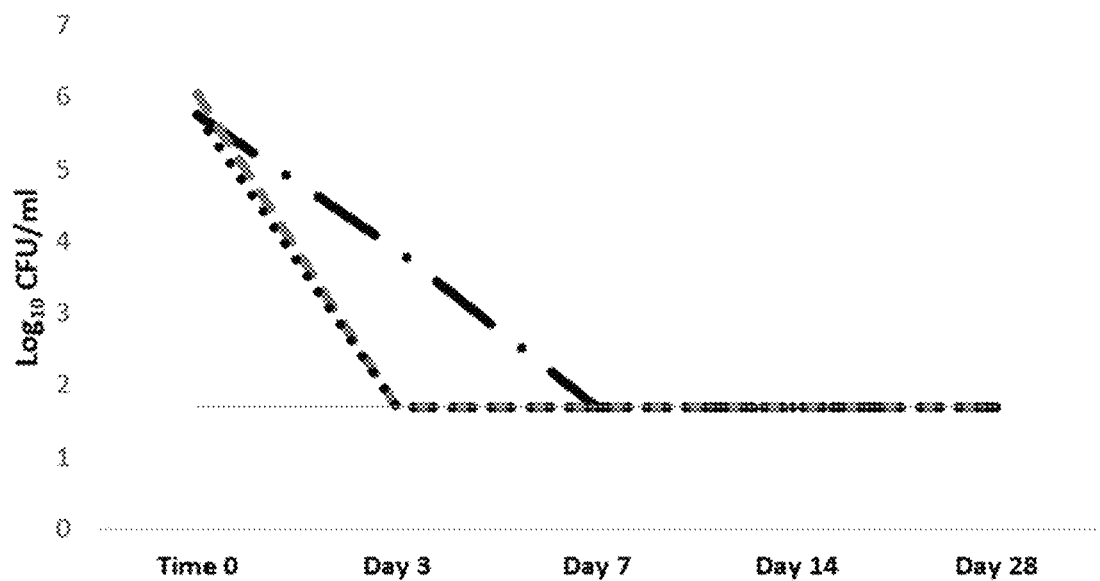
FIG. 3A to FIG. 3F depict graphs of the effect on microorganisms of exposure to different compositions.
Figure 3B:
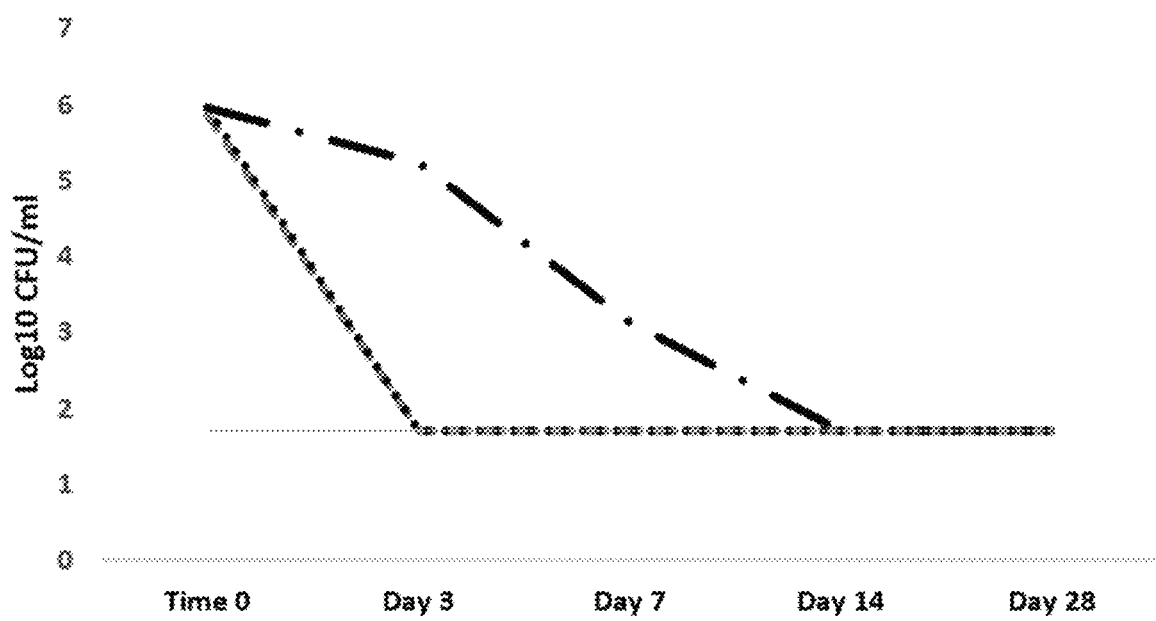
Figure 3C:
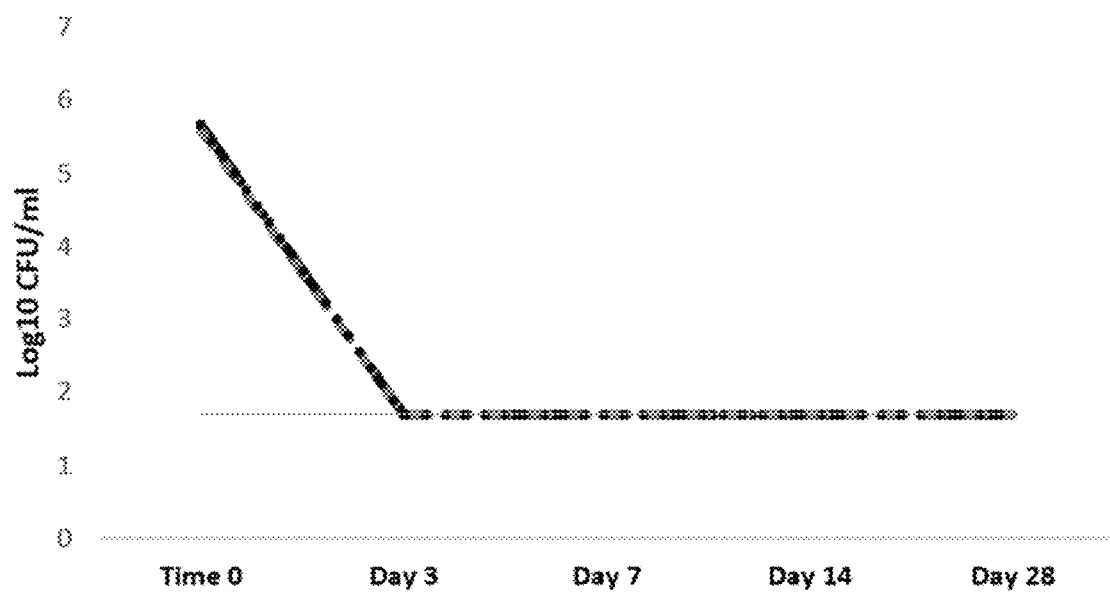
Figure 3D:
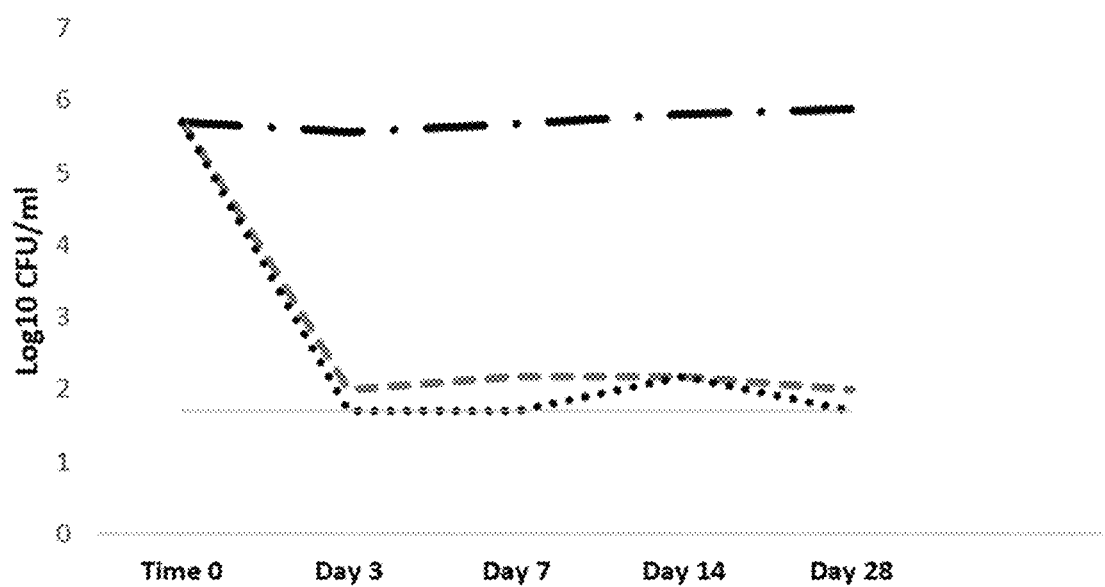
Figure 3E:
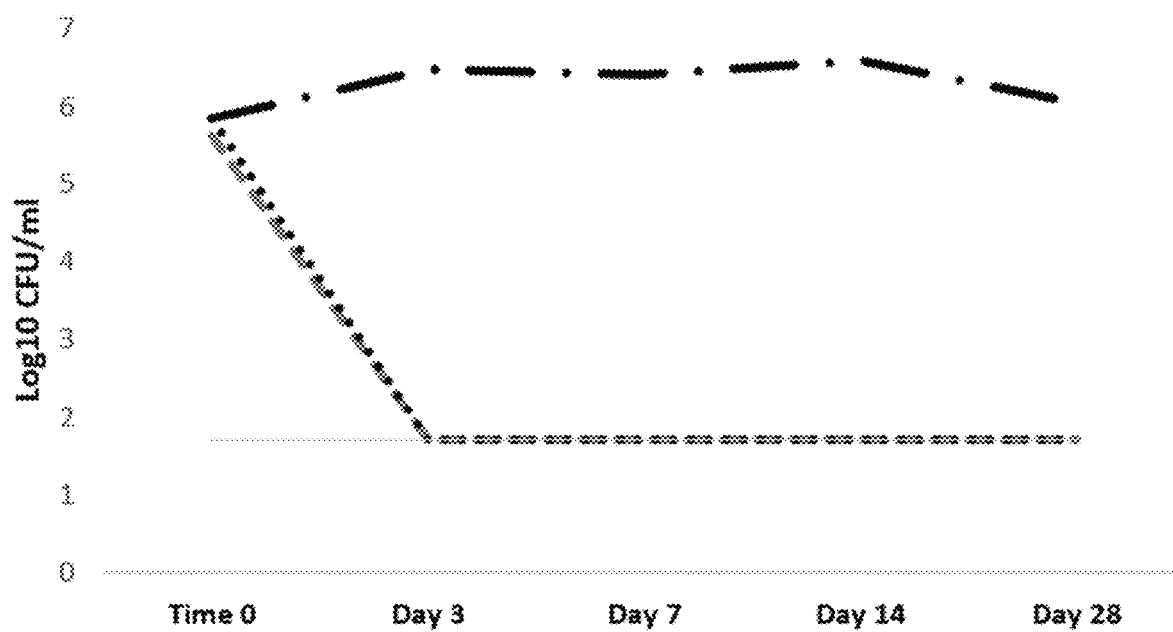
Figure 3F:
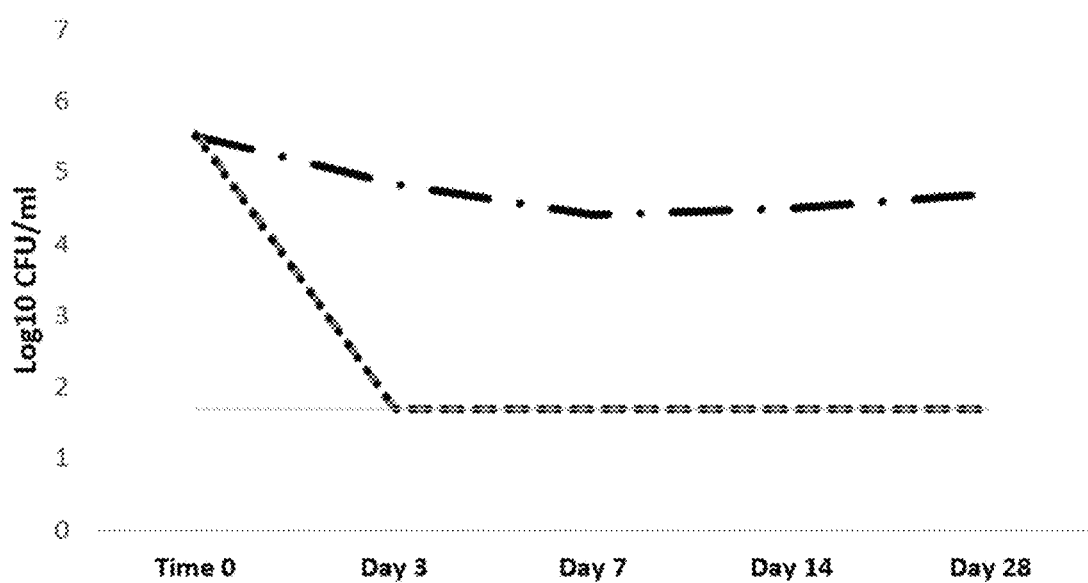

This example illustrates the surface disinfection properties of aminoguanidine-cuminaldehyde hydrazone (CG, R'=iPr; (2E)-2-{[4-(propan-2-yl)phenyl]methylidene}hydrazine-1-carboximidamidium. FIG. 2 shows the results of this inventive formulation with benzalkonium chloride (BAC; positive control) and water (negative control).

Tile surface disinfectant tests. Surface sanitation tests were adapted from ASTM Test Method E1153. Test bacteria (*Escherichia coli* ATCC 15597 and *Pseudomonas aeruginosa* ATCC 9027; American Type Culture Collection, Manassas, Va.) were streaked from frozen stock culture onto Mueller-Hinton agar (MHA; Sigma-Aldrich, St Louis, Mo.) and incubated at 30-37° C. for 2-4 days to produce isolated colonies. Two to three representative colonies were picked and transferred to 10 mL Mueller-Hinton broth (MHB; Sigma) and incubated at 37° C. overnight. Cultures underwent a maximum of 3 passes to fresh broth before being incubated for 48 h at 37° C. to be used as the inoculum. Sterile, glazed 2×2-inch ceramic tiles were inoculated with 100 μL of 48 h culture and allowed to dry for <1 h. Spray sanitizer solutions were prepared by mixing the test compound (5) in deionized, filtered water. Benzalkonium chloride (≥95%, Sigma) or bleach solution was used as a positive control and deionized, filtered water was used as a negative control. Solutions were transferred to 250 mL spray bottles, previously checked for spray volume consistency. For each treatment, tiles were sprayed 3 times. At the designated contact time, 15 mL of Dey-Engley broth (DEB; Sigma) was poured onto the tiles. Tiles were briskly swirled 50 times with DEB to neutralize antimicrobial agents and recover bacteria. This procedure was followed in duplicate for each treatment and contact time. The sanitizer-DEB solutions were then serially diluted in phosphate-buffered saline and plated on MHA. MHA plates were incubated at 37° C. for 18-24 h and colonies enumerated. To determine log reduction, bacteria recovered from treated tiles were compared to bacteria recovered from 2-3 replicate inoculated, untreated tiles. At high microbial levels ($4\times10^6$ CFU/mL *P. aeruginosa* ATCC 9027), sodium hypochlorite (200 ppm) caused reductions of 97.44% at 15 seconds, >99.998% at 5- and 10-min. Under identical conditions, compound 5 (500 ppm) exhibited similar activity (98.32% at 15 seconds, 99.98 and 99.995% at 5- and 10-min).

EXAMPLE 5

This example illustrates that CG exhibits broad spectrum suitability (passes USP-51) in a spray cleaning formulation alone, and in combination with sodium benzoate (0.2% total active).

The effect of CG on mold, bacteria, and yeast were tested following the USP <51> procedure. To determine preservative efficacy, the materials were analyzed at MICROCHEM Laboratory (Round Rock, Tex., USA), following the USP <51> protocol and met the key criteria for the study to be scientifically defensible. For the instant examples, the criteria for passing the USP 51 preservative efficacy protocol against bacteria is a reduction of not less than 2-log 10 from the initial count at 14 days, and no increase from the 14 day count at 28 days. The criteria for passing the USP 51 preservative efficacy protocol against yeast and mold is no increase from the initial count at 14 days and at 28 days. No increase is defined as not more than 0.5 log 10 higher than the previous value.

Cuminaldehyde Guanylhydrazone (CG) was evaluated alone and in combination with other compounds in a nonionic spray cleaner base lacking additional preservatives. Samples with 0.2% CG passed the USP 51 preservative efficacy protocol against bacteria, yeast, and mold while the unpreserved spray cleaner base control failed for several organisms. As seen in FIG. 3A to 3F, low levels of CG (0.2 wt. %), and CG (0.1 wt. %) in combination with sodium benzoate (0.1 wt. %) showed greater than 3 log reduction for all 6 organisms tested (*E. coli, S. aureus, P. aeruginosa, A. brasiliensis, B. cepacia*, and *C. albicans*). Sodium benzoate and CG alone (0.1%) did not eliminate mold to nondetectable levels under identical conditions (<2 and <4-log reductions, respectively).

This example shows that CG passed the USP 51 preservative efficacy protocol against bacteria, yeast, and mold.

EXAMPLE 6

This example illustrates that CG rapidly eliminated Gram-positive and -negative bacteria from surfaces, and in suspension. CG enhanced the antimicrobial activity of two commercial spray cleaners (All Purpose, Nonionic Spray Cleaner). Activity was enhanced when CG was used in combination with other ingredients (caprylhydroxamic acid, C2G, 43IMP).

MICROCHEM Laboratories completed the AOAC Use dilution, semi-quantitative test method against the 3 strains of bacteria using the maximum contact time of ten minutes with three replicates from the same sample submission. For the *S. aureus* testing, MICROCHEM Laboratories followed ASTM E2315 method with a 10 minute exposure but only a single replicate was tested. The ASTM E2315 quantitative test method was used by MICROCHEM Laboratories to access the performance of a single replicate of the test compounds against the MS2 virus using a 10 minute contact time.

The killing efficacy of Cuminaldehyde Guanylhydrazone (CG) in water against three bacteria was evaluated using the AOAC Use Dilution test. While a passing kill rate against *Pseudomonas aeruginosa*, and a close to, but just below the target kill rate, for *Salmonella enterica* were detected, a kill rate against *Staphylococcus aureus* was not achieved. The test results were the same for both concentrations tested (0.2 wt. % and 0.5 wt. %). Table 9, below presents the results.

TABLE 9

Results of AOAC International Test Method Against Bacteria

| Test Microorganism | Test Substance | Carriers Tested | Confirmed Positive | Result |
|---|---|---|---|---|
| P. aeruginosa | CG 0.2 wt. % | 60 | 2 | Pass (6) |
| ATCC 15442 | CG 0.5 wt. % | 60 | 2 | Pass (6) |
| S. aureus | CG 0.2 wt. % | 60 | 12 | Fail (3) |
| ATCC 6538 | CG 0.5 wt. % | 60 | 12 | Fail (3) |
| S. enterica | CG 0.2 wt. % | 60 | 2 | Fail (2) |
| ATCC 10708 | CG 0.5 wt. % | 60 | 2 | Fail (2) |

Additional testing was done against *S. aureus* using the suspension time kill procedure ASTM E2315 to see if CG would be effective with other ingredients in the test formulation. Several combinations were identified that worked better to rapidly eliminate *S. aureus* with CG present at 0.2 wt. % than by themselves. The addition of 0.2 wt. % CG also boosted the killing power of a nonionic spray cleaner, an all-purpose cleaner, and a surfactant control base. An additional modified ASTM E2315 test of a subset of these same formulations failed to significantly reduced MS2 virus levels versus the controls.

The results of E2315 Testing of cuminaldehyde guanylhydrazone and controls against *S. aureus* ATCC 6538 with 10 minute contact time are shown in Table 10, below. In this table, the Average Percent Reduction and Average $\text{Log}_{10}$ Reduction are compared to Time Zero Control.

TABLE 10

Average Effect of Treatment with CG and Controls on *S. aureus*

| Test Substance | CFU/mL | Percent Reduction | $\text{Log}_{10}$ Reduction |
|---|---|---|---|
| Test Control | 2.15E+06 | NA | NA |
| Nonionic spray cleaner | 1.35E+06 | 47.06 | 0.28 |
| 0.2 wt. % CG in nonionic spray cleaner | 2.10E+02 | 99.99 | 4.08 |
| All-Purpose cleaner (pH 9.5-10, nonionic) | 9.50E+05 | 62.75 | 0.43 |
| 0.2 wt. % CG in All-Purpose Cleaner | 2.45E+04 | 99.04 | 2.02 |
| Surfactant Control | 1.47E+06 | 31.67 | 0.18 |
| 0.2 wt. % CG in Surfactant Control (SC) | 3.90E+03 | 99.81 | 2.73 |
| 0.5 wt. % capryl hydroxamic acid in SC | 2.13E+06 | −7.44 | −0.02 |
| 0.5 wt. % capryl hydroxamic acid + 02. wt. % CG in SC | 3.33E+01 | 99.99 | 5.08 |
| 0.15 wt. % C2G in SC | 1.30E+06 | 36.40 | 0.20 |
| 0.15 wt. % C2G + 0.2 wt. % CG in SC | 3.02E+04 | 98.50 | 2.90 |
| 0.10 wt. % 43IMP in SC | 2.43E+06 | −20.38 | −0.08 |
| 0.10 wt. % 43IMP + 0.2 wt. % CG in SC | 1.42E+05 | 95.68 | 2.95 |
| Thymol-based disinfectant cleaning prep. | <5.00E+00 | >99.99 | >5.71 |

This example shows that addition of 0.2 wt. % CG to non-ionic spray cleaner; all-purpose cleaner; surfactant control; 0.5 wt/% capryl hydroxamic acid; 0.15 wt. % C2G in SC; or 0.10 wt. % 43IMP in SC increases the average percent reduction to over 95%, a level similar than that produced by a thymol-based disinfectant cleaning preparation. This example also shows that average Log 10 reduction as compared to Time Zero control increased with the addition of 0.2 wt. % CG, and in the case of 0.5 wt. % capryl hydroxamic acid+02. wt. % CG in SC, to a level nearly as high as that of a thymol-based disinfectant cleaning preparation.

EXAMPLE 7

Antiviral testing (10 min contact time) of CG-containing formulas against MS-2 Bacteriophage ATCC 15597-B1 and human coronavirus, Strain 229E, ATCC VR-740. CG and compositions did not show enhanced antiviral activity relative to the base formula.

Two additional tests were conducted to see the effect of CG and CG in combination with other potential biocides against MS2 Bacteriophage ATCC 15597-B1 and Human Coronavirus, Strain 229E, ATCC VR-740. In both tests, none of the treatments showed significant increased killing over the control solution. The results of E2315 testing of CG and controls against MS2 Bacteriophage ATCC 15597-B1 with a 10 minute contact time are shown in Table 11, below. The results for E1052 testing of CG and controls against Human Coronavirus, Strain 229E, ATCC VR-740 with a 10 minute contact time are shown in Table 12, below.

TABLE 11

Average Effect of Treatment with CG and Controls on ATCC 155597-B1

| Test Substance | PFU/mL | % Reduction | $\text{Log}_{10}$ Reduction |
|---|---|---|---|
| Test Control | 8.28E+08 | NA | NA |
| Nonionic spray cleaner | 3.00E+07 | 96.38% | 1.44 |
| 0.2 wt. % CG in nonionic spray cleaner | 7.25E+06 | 99.12% | 2.06 |
| 0.5 wt. % capryl hydroxamic acid + 02. wt. % CG | 1.23E+07 | 98.51% | 1.83 |
| 0.15 wt. % C2G + 0.2 wt.% CG | 9.50E+06 | 98.85% | 1.94 |
| 0.10 wt. % 43IMP + 0.2 wt. % CG | 9.40E+06 | 98.86% | 1.94 |
| Surfactant Control | 9.10E+06 | 98.90% | 1.96 |

TABLE 12

Average Effect of CG and Controls Against Human Coronavirus

| Test Substance | *$\text{TCID}_{50}$ per 0.1 mL $\text{Log}_{10}$ | $\text{Log}_{10}$ Reduction | Percent Reduction |
|---|---|---|---|
| Test Control | 5.25 | | NA |
| Nonionic spray cleaner | ≤2.50 | ≥2.75 | ≥99.82 |
| 0.2 wt. % CG in nonionic spray cleaner | ≤2.50 | ≥2.75 | ≥99.82 |
| 0.5 wt. % caprylhydroxamic acid + 0.2 wt. % CG | ≤3.50 | ≥1.75 | ≥98.22 |
| 0.15 wt. % C2G + 0.2 wt. % CG | ≤3.50 | ≥1.75 | ≥98.22 |
| 0.10 wt. % 43IMP + 0.2 wt. % CG | ≤3.50 | ≥1.75 | ≥98.22 |
| Surfactant Control | | Not tested | |

*Tissue Culture Infective Dose (TCID50) represents the endpoint dilution where 50% of the cell cultures exhibit cytopathic effects due to infection by the test virus.

This example shows that addition of 0.2 wt. % CG does not have much of an effect on the disinfection ability of non-ionic spray cleaner; 0.5 wt. % caprylhydroxamic acid; or 0.10 wt. % 43IMP against MS2 bacteriophage or Human coronavirus.

EXAMPLE 8

This example illustrates that, when combined with different commercial products, Cuminaldehyde Guanylhydrazone (CG) was stable in at least 4 different classes of household products including nonionic spray cleaners, polishes, hand soap, and liquid dish soap.

Freeze-thaw studies were conducted using a commercial refrigerator freezer and were completed over a two week period where the samples were frozen, thawed and observed for 3 cycles. Additional samples were stored in 15 mL Falcon tubes in the refrigerator, at room temperature and in a 40° C. oven. These samples were removed and evaluated at three time points in conjunction with the freeze-thaw samples. The compositions of the household products in which CG was stable are listed below in tables 13 and 14. The "Surfactant Control" was composed as follows: 4% 1,3-propanediol, 4% alkyl polyglucoside (C8-C16), 2% ethoxylated fatty alcohol (Clariant Genapol LA 070), 90% deionized water.

TABLE 13

Composition of Household Products in Which CG was Stable

| Shower Spray | Hand Wash (gel) | Dish Soap |
|---|---|---|
| water | water | water |
| lactic acid | glycerin | sodium lauryl sulfate |
| decyl glucoside | sodium chloride | lauramine oxide |
| potassium hydroxide | sodium citrate | decyl glucoside |
| lauryl glucoside | sodium lauryl sulfate | lauryl glucoside |
| c12-16 pareth-7 | citric acid | agrumex |
| linalool | tocopheryl acetate | benzyl acetate |
| methyl-chloroiso-thiazolinone | aloe barbadensis extract | cyclamen aldehyde |
| methyliso-thiazolinone | colorant | dihydro myrcenol |
| sodium carbonate | fragrance (parfum) | dipropylene glycol |
|  | decyl glucoside, lauryl glucoside | hedione |
|  | cocamidopropyl betaine | hedione |
|  | cocamidopropyl hydroxysultaine | hexyl cinnamic aldehyde |
|  | methylisothiazolinone | iso e super |
|  | methylchoroiso-thiazolinone | linalool |
|  |  | linalyl acetate |
|  |  | phenyl ethyl alcohol |
|  |  | ethanol |
|  |  | glycerin |
|  |  | sodium chloride |
|  |  | proprietary colorant |
|  |  | citric acid |
|  |  | methylchloroiso-methylisothiazolinone |

TABLE 14

Composition of Polish Products in Which CG was Stable

| Stainless Steel Polish | Wood Polish | Granite Polish |
|---|---|---|
| water | water | water |
| propanediol | glycerin | capryleth-4 |
| ethanol | peg 400 dioleate | ethanol |
| cocamidopropyl betaine | dimethicone | limonene |
| phenoxyethanol | oleic acid | linalool |
| decyl glucoside | acrylic polymer(s) | methylisothiazolinone |
| lauryl glucoside | benzaldehyde | octylisothiazolinone |
| limonene | dipropylene glycol | sodium citrate |
| glycerin | galaxolide |  |
| methylisothiazolinone | potassium hydroxide |  |
| benzylisothiazolinone | methylisothiazolinone |  |
| octylisothiazolinone |  |  |

Cuminaldehyde Guanylhydrazone (CG) was added to several different commercial products. Stability testing was performed in refrigerator (2.8° C.), at room temperature (21.1° C.), in an oven (40° C.), and through 3 freeze-thaw cycles. It was determined that CG was stable in at least 4 different classes of household products including nonionic spray cleaners, polishes, hand soap, and liquid dish soap. Instabilities and/or phase separations were seen in several different products. Not intending to be theory-bound, these instabilities may be attributed mainly to carbonate, anionic surfactants, or high pH. Experiments to identify and overcome the cause of the incompatibilities indicated that a carbonate-free formula, or the incorporation of an emulsifier prevented some of the instabilities and phase separations seen.

EXAMPLE 9

This example illustrates that Cuminaldehyde Guanylhydrazone (CG), Ocylbenzaldehyde Guanylhydrazone (OBG), and Benzaldehyde Guanylhydrazone (BG), when combined with a nonionic spray cleaner are able to maintain an over 5 log reduction of *A. brasiliensis*.

The method used to determine the extended preservative efficacy of CG followed the guidelines of USP51, but the test was extended to 97 days and an aliquot of the sample was reinoculated with *Aspergillus brasiliensis* after 36 days, and then tested out an additional 60 days. The 4-Ocylbenzaldehyde Guanylhdrazone sample was not compatible in water so was tested in propane diol instead. The samples were stored in a GYROMAX 74&R 30° C. oven after inoculation until the study was completed.

Cuminaldehyde Guanylhydrazone (CG) and other compounds were evaluated for preservative efficacy in both a nonionic spray cleaner base and water lacking additional preservatives for 97 days. As seen in Table 15, below, the results were very impressive. The three samples containing CG, the sample containing 4 Ocylbenzaldehyde Guanylhydrazone (OBG), and the sample containing Benzaldehyde Guanylhydrazone (BG) all maintained an over 5 log reduction of *A. brasiliensis* CFU/mL from the time zero concentration at all 5 measurement points. These values were also over a 3-5 log reduction of the two controls; spray cleaner base and water.

TABLE 15

CFU/mL Effect on *A. brasiliensis*

| Time | | Log 10 Reduction | | | | |
|---|---|---|---|---|---|---|
|  | Zero | Day 5 | Day 14 | Day 37 | Day 61 | Day 97 |
| Shower Spray + | 4.1 × 10⁵ | 0.6 | 0.8 | 1.0 | 1.3 | 2.6 |
| CG 0.2% + | 4.1 × 10⁵ | 5.6 | 5.6 | 5.6 | 5.6 | 5.6 |
| CG 0.4% + | 4.1 × 10⁵ | 5.6 | 5.6 | 5.6 | 5.6 | 5.6 |
| CG 0.2%, 0.2% Benzoate + | 4.1 × 10⁵ | 5.6 | 5.6 | 5.6 | 5.6 | 5.6 |
| OBG 0.2% + | 4.1 × 10⁵ | 5.6 | 5.6 | 5.6 | 5.6 | 5.6 |
| BG 0.2% | 4.1 × 10⁵ | 5.6 | 5.6 | 5.6 | 5.6 | 5.6 |
| H2O | 4.1 × 10⁵ | 0.6 | 0.9 | 0.3 | 0.9 | 2.2 |
| CG 0.2% in H₂0 | 4.1 × 10⁵ | 5.6 | 5.6 | 5.6 | 5.6 | 5.6 |
| OBG 0.2% in propane diol | 4.1 × 10⁵ | 5.6 | 5.6 | 5.6 | 5.6 | 5.6 |
| BG 0.2% in H20 | 4.1 × 10⁵ | 5.6 | 5.6 | 5.6 | 5.6 | 5.6 |

After 36 days, 4 mL of each sample were placed in a separate Falcon tube and reinoculated with *A. brasiliensis*. These samples were also measured for Log 10 reduction of CFU/mL over 60 days with 3 data points. As seen in Table 16, all samples provided a 2.8 to 5.6 Log 10 reduction of CFU/mL over the test period, and a 1.8 to 4.6 Log 10 reduction over the spray cleaner control. Unfortunately, the water control picked up bacterial contamination and the mold colonies could not accurately be recorded. These results showed that the samples continued to provide efficacy against a re-challenge of *A. brasiliensis*.

TABLE 16

CFU/mL Effect on *A. brasiliensis* Reinoculated After 36 Days

| Time | | | Log 10 Reduction | | |
|---|---|---|---|---|---|
|  | zero | reinoculated | Day 10 | Day 28 | Day 60 |
| Shower Spray + | 4.1 × 10⁵ | 3.7 × 10⁵ | 1.0 | 1.0 | 1.7 |
| CG 0.2% + | 4.1 X10⁵ | 3.7 × 10⁵ | 5.6 | 5.6 | 5.6 |
| CG 0.4% + | 4.1 X10⁵ | 3.7 × 10⁵ | 5.6 | 5.6 | 5.6 |
| CG 0.2%, 0.2% Benzoate + | 4.1 X10⁵ | 3.7 × 10⁵ | 2.8 | 5.6 | 5.6 |
| OBG 0.2% + | 4.1 X10⁵ | 3.7 × 10⁵ | 3.0 | 5.6 | 5.6 |
| BG 0.2% | 4.1 X10⁵ | 3.7 × 10⁵ | 3.3 | 5.6 | 5.6 |

TABLE 16-continued

CFU/mL Effect on *A. brasiliensis* Reinoculated After 36 Days

| | Time | | Log 10 Reduction | | |
|---|---|---|---|---|---|
| | zero | reinoculated | Day 10 | Day 28 | Day 60 |
| H₂0 | 4.1 × 10⁵ | 3.7 × 10⁵ | TNC* | TNC* | TNC* |
| CG 0.2% in H20 | 4.1 X10⁵ | 3.7 × 10⁵ | 2.8 | 5.6 | 5.6 |
| OBG 0.2% in propane diol | 4.1 X10⁵ | 3.7 × 10⁵ | 5.6 | 5.6 | 5.6 |
| BG 0.2% in H20 | 4.1 X1⁺⁵ | 3.7 × 10⁵ | 5.6 | 5.6 | 5.6 |

*Bacterial Contamination.

EXAMPLE 10

This example illustrates that Cuminaldehyde Guanylhydrazone (CG), when combined with a nonionic bathroom spray cleaner base lacking additional preservatives significantly reduced *Aspergillus brasiliensis* in the sample for at least 28 days.

Cuminaldehyde Guanylhydrazone (CG) was evaluated alone in a nonionic bathroom spray cleaner base lacking additional preservatives with a pH range of 7 to 8. Although a precipitate formed upon addition of CG, there was still a significant reduction of *Aspergillus brasiliensis* in the sample containing 0.2 wt. % CG over the 28-day test. The presence of sodium citrate is speculated to be the cause of the precipitate.

The test method used to evaluate the effect on nonionic bathroom spray cleaner base lacking additional preservatives was based on the USP51 protocol and was conducted over 28 days of incubation in a 30° C. oven. The theoretical starting concentration in the unpreserved base was $5 \times 10^{-5}$ and that was used as the time zero value as an initial count at time zero was not completed. The results are shown on Table 17, below. This table shows that bathroom spray base with 0.1 wt. % CG reduces *A. brasiliensis* by 2.85 Log 10 CFU/mL at 28 days. This table also shows that bathroom spray base with 0.2 wt. % CG reduces *A. brasiliensis* by 2.74 Log 10 CFU/mL by day 2; and 5.70 Log 10 CFU/mL at 9 and 28 days.

TABLE 17

Reduction of *A. brasiliensis* in bathroom spray with CG

| | Log10 Reduction (CFU/mL) | | |
|---|---|---|---|
| Sample | Day 2 | Day 9 | Day 28 |
| Bathroom Spray Base (BS) | 0 | 0 | 0 |
| BS + 0.1 wt. % CG | 0 | 0 | 2.85 |
| BS + 0.2 wt. % CG | 2.74 | 5.70 | 5.70 |

EXAMPLE 11

This example illustrates that a spray cleaner with 0.2 wt. % CG impedes growth of *A. brasiliensis* for at least eight days.

A real-life example test was conducted in which a tile was treated with a spray cleaner with 0.2 wt. % CG, or with a hydrogen peroxide-containing all-purpose cleaner. After drying for 5 minutes the tile was then inoculated with two agar plugs with actively growing *A. brasiliensis*. After eight days, a dramatic difference could be seen in the CG-treated tile where no growth was seen versus the all-purpose cleaner treated tile which had numerous new colonies of mold growing on it. This indicated that a spray cleaner with 0.2 wt. % CG added could provide an extended mold-killing benefit as compared to a commercial all-purpose cleaner with hydrogen peroxide product.

This test method was developed in the USDA-ARS lab as a simulation of what might occur in a consumer's bathroom with actively growing mold. The application involved spraying a tile with product, allowing 5 minutes for it to dry, followed by tilting the tile to allow any undried product to roll off, and then finished drying by blotting with a KIM-WIPE paper absorbent tissue (Kimberly Clark Worldwide Inc.; Neenah, Wis.). The tile was placed in a petri plate, then wetted with 3 squirts of DI water, two small plugs of agar with actively growing *A. brasiliensis* were placed on top of the tile, and then covered by the top of the petri plate. When no growth was observed after 2 days, 1 ml of Mueller Hinton broth was gently added on the tile, and an additional 1 mL in the petri plate at the base of the tile. The samples were photographed after 8 days.

Therefore, this disclosure relates to novel antimicrobial blends developed using moderately hydrophobic hydroxamic acids and guanylhydrazones. Several combinations were surprisingly synergistic in their biocidal activity and provide complementary broad-spectrum antimicrobial activity, unexpectedly even in formulas containing typically deactivating anionic and amphoteric surfactants. This inventive composition is the first example of broad spectrum, synergistic combined bactericidal and fungicidal activity arising from the disclosed combinations of guanylhydrazones and hydroxamic acids.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety, including any materials cited within such referenced materials. In addition to the citations above, the contents of the following references are also incorporated herein by reference in their entirety: US 2018/0303100. Furthermore, the invention encompasses any possible combination of some or all of the various embodiments and characteristics described herein and/or incorporated herein. In addition, the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 30%, preferably by as much as 20%, and more preferably by as much as 10% to a reference quantity, level, value, or amount.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims. Although any methods and materials similar or equivalent to those described herein can be used in the practice or testing of the present invention, the preferred methods and materials are herein described. Those skilled in the art may recognize other equivalents to the specific embodiments described herein which equivalents are intended to be encompassed by the claims attached hereto.

The claimed invention is:

1. A composition comprising: a blend of one organic acid and one water-soluble hydrazone, wherein said organic acid is a hydroxamic acid, a carboxylic acid, or a mixture thereof, and wherein the blend exhibits biological activity that is synergistic when compared to a sum of a biological activity of said organic acid and a biological activity of said hydrazone.

2. The composition of claim 1, wherein said organic acid is a hydroxamic acid and has the following formula:

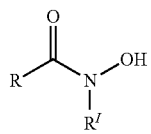

wherein R is aryl or alkyl, and wherein $R^1$ is H, aryl, or alkyl.

3. The composition of claim 1, wherein said organic acid is a hydroxamic acid and has the following formula:

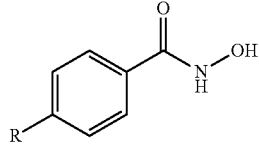

wherein R is H, methyl, ethyl, propyl, isopropyl, or butyl.

4. The composition of claim 1, wherein said organic acid is a hydroxamic acid i-s-selected from the group consisting of: salicylhydroxamic acid, N-hydroxysuccinimide, benzhydroxamic acid, O-methylhydroxylamine HCl, O-benzylhydroxylamine HCl, N-benzylhydroxylamine HCl, O-tert-butylhydroxylamine HCl, acetohydroxamic acid, suberohydroxamic acid, O-ethylhydroxylamine HCl, O-phenylhydroxylamine HCl, caprylhydroxamic acid, N-hydroxymaleimide, and combinations thereof.

5. The composition of claim 1, wherein said organic acid is caprylhydroxamic acid.

6. The composition of claim 1, wherein said organic acid is a carboxylic acid.

7. The composition of claim 1, wherein said organic acid is a mixture of at least one carboxylic acid and at least one hydroxamic acid.

8. The composition of claim 1, wherein said hydrazone comprises an aryl guanylhydrazone.

9. The composition of claim 1, wherein said hydrazone comprises a self-assembled complexation of at least one aminoguanidine and at least one aldehyde.

10. The composition of claim 1, wherein said hydrazone comprises a self-assembled complexation of an aminoguanidine and an aldehyde having the following formula:

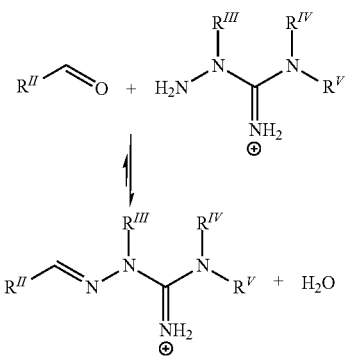

wherein $R^{II}$, $R^{III}$, and $R^{IV}$ are independently H, aryl, or alkyl; and $R^V$ is H, aryl, alkyl, $NH_2$, or $NCHR^{II}$.

11. The composition of claim 10, wherein the aminoguanidine, the aldehyde, and the hydrazone exist in equilibrium in the blend.

12. The composition of claim 1, wherein said hydrazone comprises a self-assembled complexation of an aminoguanidine and an aldehyde having the following the formula:

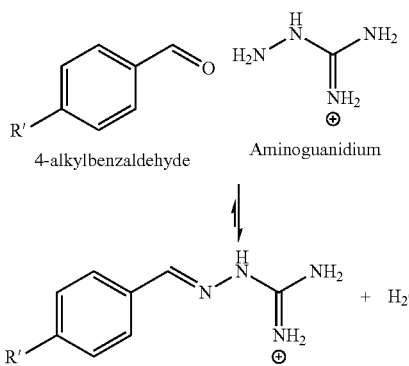

wherein $R^1$ is H or octyl.

13. The composition of claim 12, wherein the aminoguanidine, the aldehyde, and the hydrazone exist in equilibrium in the blend.

14. The composition of claim 1, wherein the biological activity exhibited by the blend includes antibacterial activity.

15. The composition of claim 1, wherein the biological activity exhibited by the blend includes antifungal activity.

16. The composition of claim 1, wherein the biological activity exhibited by the blend includes both antibacterial activity and antifungal activity.

17. The composition of claim 1, wherein the blend is a component of a formulation and the effective amount of said hydroxamic acid and said hydrazone within the formulation is less than about 2 wt % of the total formulation.

18. A formulation containing the blend of claim 1.

19. The formulation of claim 18 selected from-foamy and non-foamy handwashes; dishwashing liquids; household cleaning sprays; laundry detergents; personal care products; cleaning concentrates; spray and non-spray cleaners; adhesives and coatings; industrial cleaner; livestock treatments; medical devices; pesticide compositions for crops; disinfectants for food processing; and preservatives for food and non-food agricultural products.

20. The formulation of claim 18, wherein the formulation further comprises a surfactant.

21. The formulation of claim 19 selected from lotions, body washes, shampoos, dilutable concentrates, sanitizers, disinfectants, odor control agents, livestock hoof dips, utter dips, oral antibiotics, topical antiseptics, odor control, and feed additives.

22. A method of reducing bacterial and fungal contamination, the method comprising applying the composition of claim 1 to a designated area or object suspected of having bacterial or fungal contamination.

23. The method of claim 22, wherein reducing bacterial and fungal contamination comprises at least one of sanitizing, reducing odor, controlling fragrance, extending shelf-life, and reducing mildew.

24. The method of claim 22, wherein said bacteria are selected from the group consisting of: *Escherichia coli, Pseudomonas aeruginosa, Staphylococcus aureus, Listeria monocytogenes, Salmonella, Burkholderia cepacia, Clostridium difficile, Streptococcus, Vibrio, Bacillus, Campylobacter, Chlamydia, Listeria, Neisseria, Treponema*, and combinations thereof.

25. The method of claim 22, wherein said fungi are selected from the group consisting of: *Aspergillus brasiliensis, Aspergillus fumigatus, Candida albicans, Candida auris*, and combinations thereof.

* * * * *